United States Patent
Paldus et al.

(10) Patent No.: US 7,265,842 B2
(45) Date of Patent: Sep. 4, 2007

(54) METHOD FOR DETECTING A GASEOUS ANALYTE PRESENT AS A MINOR CONSTITUENT IN AN ADMIXTURE

(75) Inventors: Barbara Paldus, Portola Valley, CA (US); Bruce Richman, Sunnyvale, CA (US); Alexander Kachanov, Sunnyvale, CA (US); Eric Crosson, Sunnyvale, CA (US)

(73) Assignee: Picarro, Inc., Sunnyvale, CA (US)

( * ) Notice: Subject to any disclaimer, the term of this patent is extended or adjusted under 35 U.S.C. 154(b) by 388 days.

(21) Appl. No.: 10/966,314

(22) Filed: Oct. 14, 2004

(65) Prior Publication Data

US 2006/0082778 A1    Apr. 20, 2006

(51) Int. Cl.
G01J 5/02      (2006.01)
G01J 1/42      (2006.01)
G01N 21/00     (2006.01)

(52) U.S. Cl. .................. 356/437; 356/436; 356/438; 250/343; 250/373

(58) Field of Classification Search ................ 356/437, 356/300, 334, 436, 438; 250/338, 339.01, 250/339.07, 339.11, 339.13, 330, 343, 373
See application file for complete search history.

(56) References Cited

U.S. PATENT DOCUMENTS

| | | | | |
|---|---|---|---|---|
| 3,723,731 A * | 3/1973 | Blau, Jr. | ...................... | 356/451 |
| 5,528,040 A * | 6/1996 | Lehmann | ..................... | 250/343 |
| 5,686,988 A * | 11/1997 | Garrett | ........................ | 356/318 |
| 5,912,740 A * | 6/1999 | Zare et al. | .................... | 356/437 |
| 6,249,343 B1 * | 6/2001 | Wang et al. | ............... | 356/243.1 |
| 6,466,322 B1 * | 10/2002 | Paldus et al. | ................ | 356/437 |
| 6,744,516 B2 * | 6/2004 | DiDomenico et al. | ....... | 356/437 |
| 6,791,086 B2 * | 9/2004 | Russell | ................... | 250/339.07 |
| 6,795,190 B1 * | 9/2004 | Paul et al. | .................... | 356/437 |
| 6,822,236 B1 * | 11/2004 | Nelson et al. | ............ | 250/338.5 |
| 2004/0164237 A1 * | 8/2004 | Jones et al. | .............. | 250/269.1 |
| 2004/0211905 A1 * | 10/2004 | Hancock et al. | ............ | 250/343 |
| 2006/0119851 A1 * | 6/2006 | Bounaix | ..................... | 356/437 |

* cited by examiner

*Primary Examiner*—Tarifur Chowdhury
*Assistant Examiner*—Daniel Cartoon
(74) *Attorney, Agent, or Firm*—Lumen Intellectual Property Services

(57) ABSTRACT

A gaseous target analyte present as a minor constituent in an admixture with at least one other gaseous species can be detected using a cavity enhanced optical spectrometer by a process comprising the steps of:
  i) identifying a plurality of strong spectral absorption peaks of the target analyte which are present within the scanning range of the spectrometer,
  ii) determining for the identified peaks the pressure region above which the peak width increases substantially with increasing pressure and below which the peak width is substantially independent of pressure,
  iii) determining which of the peaks identified in step i) are, within the pressure region determined in step ii), free from spectral interference by any of the other components of the admixture.
  iv) measuring the spectrum of the admixture at the pressure region identified in step ii).

14 Claims, 31 Drawing Sheets

Self-induced Lorentzian halfwidth plotted against pressure for the $R(3)$ line of the $H^{35}Cl$ isotopomer Foreign-induced Lorentzian halfwidth plotted against pressure for the $R(3)$ line of the $H^{35}Cl$ isotopomer, in the presence of different perturbing gases

FIGURE 6a
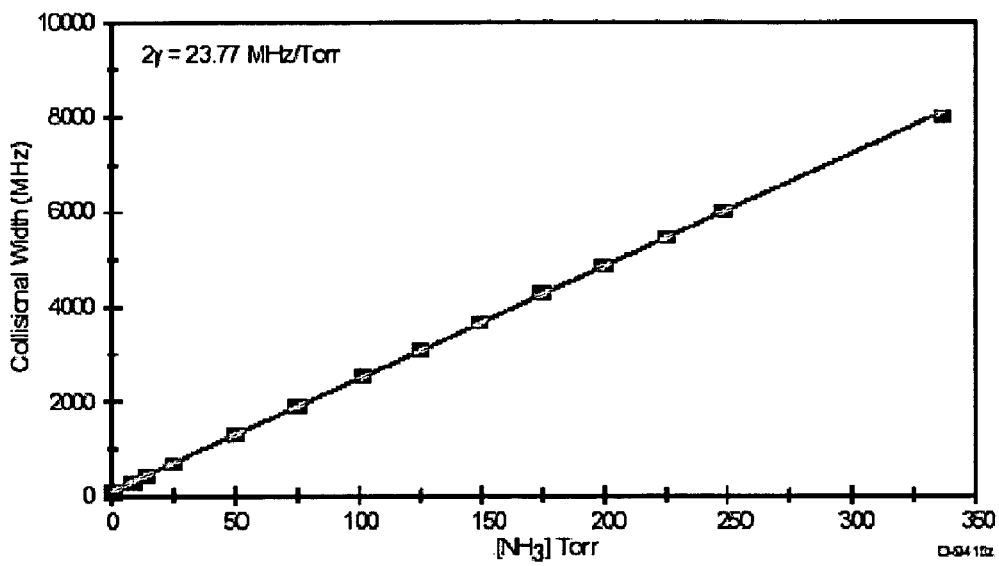
1.3925 μm water vapor absorption collisional line width versus ammonia bath gas pressure.
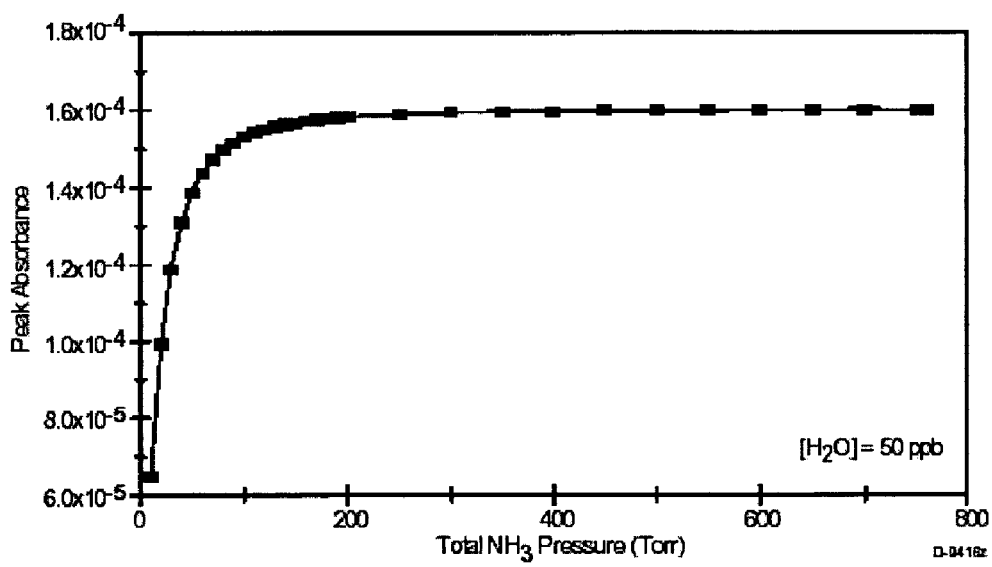
Calculated 1.3925 μm water vapor peak absorbance versus ammonia bath gas pressure.
FIGURE 6b

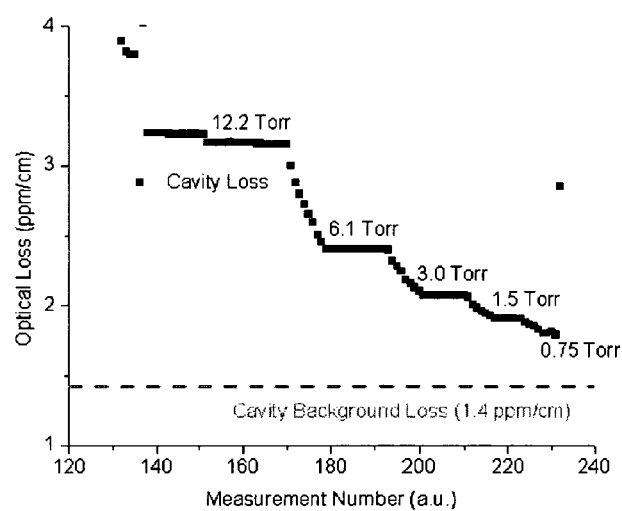
FIGURE 8a
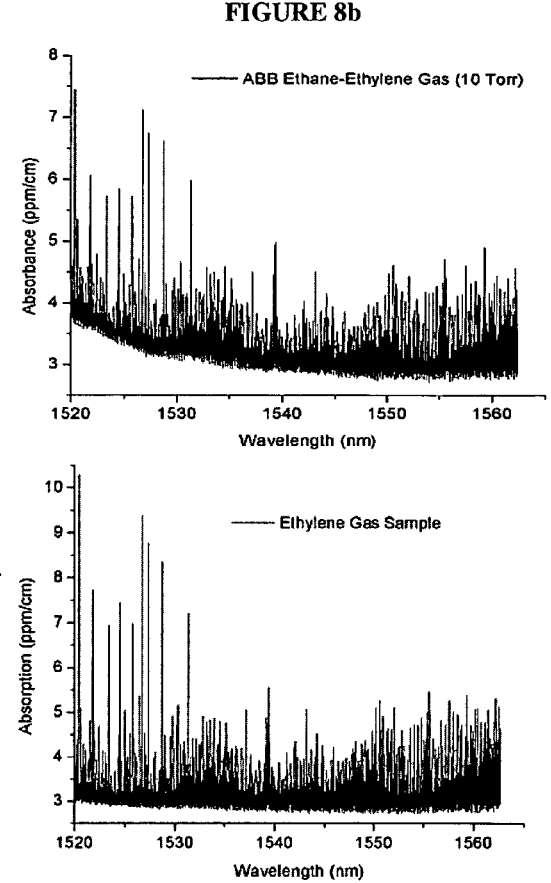
FIGURE 8b
FIGURE 8c

Detailed comparison of HITRAN and measured spectra for CO, $CO_2$ and $H_2O$ in Region 1.1.

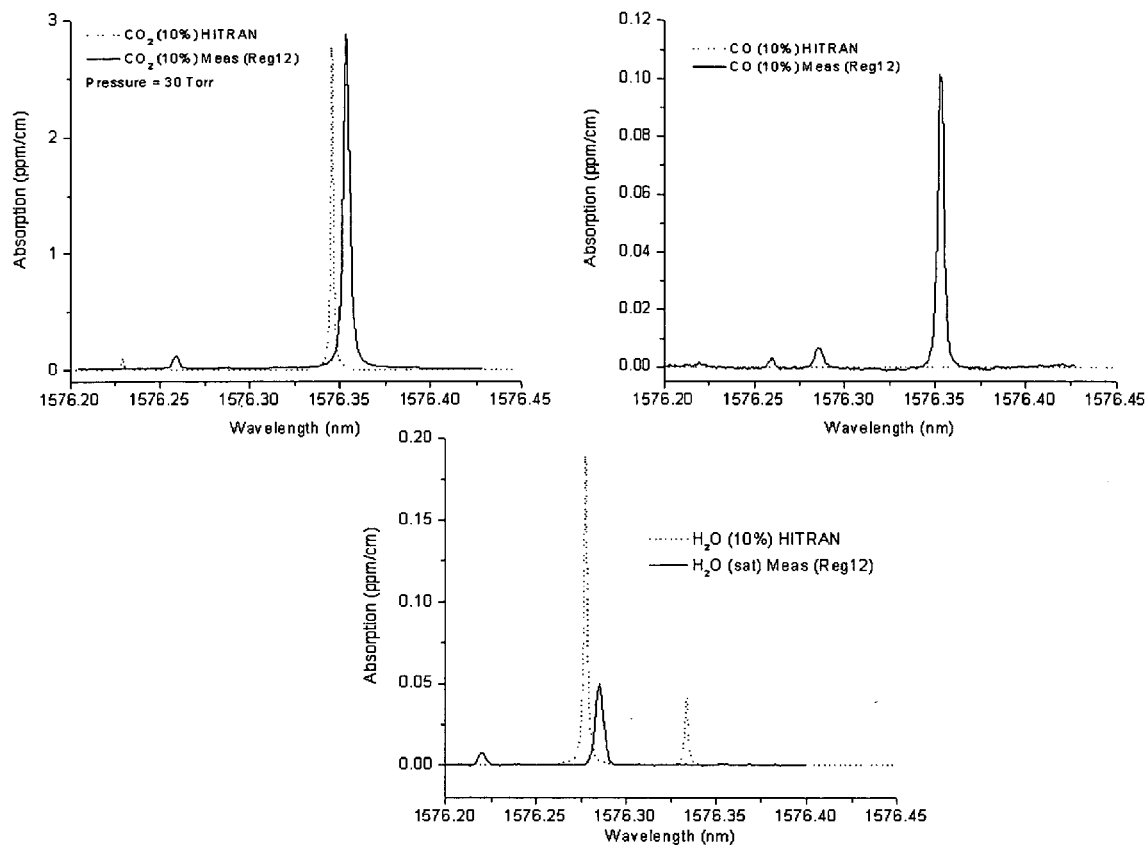
FIGURES 17a 17b and 17c

Pressure Broadening of $H_2S$ Features (Full Scan)

Pressure broadening of $H_2S$ features in Region 1.1

Pressure Broadening Coefficients for $CO_2$

Pressure broadening coefficient for $H_2S$

Measured and simulated spectra of $H_2S$ in $CO_2$ at various pressures.

Diluted $H_2S$ in $CO_2$ spectra comparing concentrations of 100 ppb, 250 ppb, and 2.5 ppm. at 50 Torr

METHOD FOR DETECTING A GASEOUS ANALYTE PRESENT AS A MINOR CONSTITUENT IN AN ADMIXTURE

FIELD OF THE INVENTION

This invention relates to the detection of gas species present in trace amounts in complex background matrices using cavity enhanced optical spectroscopy i.e., cavity ring-down spectroscopy (CRDS) cavity enhanced absorption spectroscopy (also called integrated cavity output spectroscopy (ICOS) including off-axis ICOS.

BACKGROUND OF THE INVENTION

Molecular absorption spectroscopy is a technique that uses the interaction of energy with a molecular species to qualitatively and/or quantitatively study the species, or to study physical processes associated with the species. The interaction of radiation with matter can cause redirection of the radiation and/or transitions between the energy levels of the atoms or molecules. The transition from a lower level to a higher level with an accompanying transfer of energy from the radiation to the atom or molecule is called absorption. When a molecule absorbs light, the incoming energy excites a quantized structure to a higher energy level. The type of excitation depends on the wavelength of the light. Electrons are promoted to higher orbitals by ultraviolet or visible light, vibrations are excited by infrared light, and rotations are excited by microwaves. The infrared (IR) region is generally defined as radiation with wavelength in the range from 1 to 50 µm. Frequency is a measure of the type of radiation related to wavelength such that frequency equals the speed of light divided by the wavelength. A common unit of radiation frequency is $cm^{-1}$, which is simply the reciprocal of the wavelength expressed in cm. The 0.7 to 2.5 µm wavelength region is generally called the near-infrared (NIR), the 2.5 to 15 µm wavelength region is referred to as the mid-infrared and the 15 to 50 µm wavelength region is called the far-infrared. The wavelengths of IR absorption bands are characteristic of specific types of chemical bonds, and IR spectroscopy finds its greatest utility in the identification of organic and organometallic molecules.

The data that is obtained from spectroscopy is called a spectrum and the instrument or apparatus that produces the spectrum is called a spectrometer. An absorption spectrum shows the absorption of light as a function of its wavelength. The spectrum of a particular atom or molecule depends on its energy level structure. A spectrum can be used to obtain information about atomic and molecular energy levels, molecular geometries, chemical bonds, the interactions of molecules, and related processes. Often, spectra are used to identify the components of a sample (qualitative analysis). Spectra may also be used to measure the amount of material present in a sample (quantitative analysis).

The quantum mechanical derivation of the strength of the absorption begins with the transition moment:

$$R=<X_i|u|X_j>$$

where $X_i$ and $X_j$ are the initial and final states, respectively, and u is the electric dipole moment operator: $u=u_0+(r-r_e)du/dr+\ldots$, where $u_o$ is the permanent dipole moment, which is a constant, r is the radial length of the bond for infrared absorption, and $r_e$ is the average equilibrium bond length. Because $<X_i|X_j>=0$ for $i\neq j$ according to the laws of quantum mechanics, R simplifies to:

$$R=<X_i|(r-r_e)du/dr|X_j>$$

The result is that there must be a change in dipole moment during the vibration of the atoms of a molecule for the molecule to absorb infrared radiation. There is usually no dipole moment change during symmetric stretches of symmetric molecules, so that these bonds usually do not absorb infrared radiation.

Gaseous molecules are found only in discrete states of vibration and rotation, called the ro-vibrational state. Each such state, identified by quantum numbers describing both the vibration and rotation, has a single energy which depends on said quantum numbers. In the dipole transitions described above, a single photon of radiation is absorbed, transforming the molecule from one ro-vibrational state to another. As the energies of the ro-vibrational states are discrete, so are the energies of the transitions between them.

Therefore, a photon must possess a specific energy to be absorbed by a molecule to transform it between two given ro-vibrational states. Since the energy of a photon is proportional to the frequency of the radiation of which the photon is a part (or equivalently, inversely proportional to the wavelength), only discrete frequencies (wavelengths) can be absorbed by the molecule. The set of discrete frequencies (wavelengths), often called absorption lines, at which a particular species of molecule absorbs, is called the absorption spectrum of said molecule. The width in frequency (wavelength) of each absorption line depends on the specific ro-vibrational transition, the pressure and temperature of the gas containing the molecule, and the presence of other types of molecules in said gas. Each species of molecule has a unique absorption spectrum, by which the species of molecule may be identified. Since the energies of different rotational states of a gaseous molecule are typically spaced much more closely than the energies of different vibrational states, then the absorption lines occur in sets, each set corresponding to a single vibrational transition, and many rotational transitions. These sets of absorption lines are called absorption bands. An instrument which measures an absorption spectrum is called a spectrometer.

| Functional Group Name | Bond | Spectral Range (µm) | Spectral Range ($cm^{-1}$) |
|---|---|---|---|
| Hydroxyl | O—H | 2.770-2.747 | 3610-3640 |
| Aromatic Ring | C6H6 | 3.226-3.333 | 3000-3100 |
| Alkene | C═C—H | 3.247-3.311 | 3020-3080 |
| Alkane | C—C—H | 3.378-3.509 | 2850-2960 |
| Carbonyl | C═O | 5.714-6.061 | 1650-1750 |
| Nitrile | C≡N | 4.425-4.525 | 2210-2260 |
| Amine I | N—H | 2.857-3.030 | 3300-3500 |
| Amine II | C—N | 7.353-8.475 | 1180-1360 |

Molecular vibrational bands can be likened to the acoustic frequencies of a string (such as on a violin). Similarly, molecular bands have overtones, which are harmonics of the vibrational motion. The original stretch that produces mid-infrared absorption bands is called the fundamental. A fundamental has many harmonics, as well as combinations of harmonics at a wide variety of frequencies. The absorption at the harmonics is always less than at the fundamental, and can decrease significantly for higher harmonics. Therefore, these overtone transitions are normally called weak overtones.

In the NIR, all the vibrational transitions are harmonics of fundamental, mid-infrared bands. These transitions can be one hundred to ten thousand times weaker than their mid-infrared counterparts. Standard methods, such as Fourier Transform Infrared Spectroscopy (FTIR), commonly used to characterize mid-infrared transitions, often have difficulty detecting these weak absorption features in the NIR spectral region. Therefore, more sensitive detection methods are required to measure NIR absorption features.

Moreover, because overtone bands and combinations of overtone bands often overlap in wavelength (frequency), the NIR is rich with dense bands of absorption lines. It is therefore not uncommon to find spectral regions where the same molecular species has both strong and weak transitions that are co-located in wavelength. Additionally, when it is required to identify one or more species present in a mixture of compounds it is extremely difficult to identify which absorption peak is attributable to a particular molecule.

Measuring the concentration of an absorbing species in a sample is accomplished by applying the Beer-Lambert Law. The Beer-Lambert law (also known as Beer's Law) is the linear relationship between absorbance and concentration of an absorbing species. The Beer-Lambert Law can be derived from an approximation for the absorption of a molecule by considering the molecule as an opaque disk whose cross-sectional area, $\sigma$, represents the effective area seen by a photon of frequency $\omega$. If the frequency of the light is far from the transition resonance, the area is approximately 0, and if $\omega$ is at resonance the area is a maximum. To derive the absorption in an infinitesimal slab, dz, of a sample as shown in FIG. 1, define the following parameters: $I_o$ is the intensity entering the sample at z=0, $I_z$ is the intensity entering the infinitesimal slab at z, dI is the intensity absorbed in the slab, I is the intensity of light leaving the sample, N is the density of absorbing molecules, and B is the cross-sectional area of the radiation. The total opaque area on the slab due to the absorbers is $\sigma NB$ dz. Then, the fraction of photons absorbed will be $\sigma NB(dz/B)$ so that:

$$dI/I_z = -\sigma dz$$

Integrating this equation from z=0 to z=L, the length of the sample, results in the total transmission, I:

$$ln(I) - ln(I_o) = -\sigma NL \text{ or } -ln(I/I_o) = \sigma NL.$$

By substituting the equation for molar concentration, C(moles/liter)=N(molecules/cm$^3$)*(1 mole/6.023×10$^{23}$ molecules)*1000 cm$^3$/liter and the relation between the natural and base 10 logarithms, $$2.303 * \log(x) = \ln(x),$$

the integrated equation becomes:

$$-\log(I/I_o) = \sigma(6.023 \times 10^{20}/2.303) \ CL \text{ or } -\log(I/I_o)$$
$$= A = C \epsilon_M L,$$

where $\epsilon_M = \sigma(6.023 \times 10^{20}/2.303) = \sigma 2.61 \times 10^{20}$ is the molar extinction coefficient.

Typical cross-sections and molar extinction coefficients are:

| | $\sigma$ (cm$^2$) | $\epsilon_M$ (M$^{-1}$ cm$^{-1}$) |
|---|---|---|
| Atoms | 10$^{-12}$ | 3 × 10$^8$ |
| Molecules | 10$^{-16}$ | 3 × 10$^4$ |
| Infrared | 10$^{-19}$ | 3 × 10 |
| Raman scattering | 10$^{-29}$ | 3 × 10$^{-9}$ |

The general Beer-Lambert Law is usually written as:

$$A(\lambda) = \alpha(\lambda) L = C \epsilon(\lambda) L \quad (1)$$

where $A(\lambda)$ is the measured absorbance, $\alpha(\lambda)$ is a wavelength-dependent absorption coefficient, $\epsilon(\lambda)$ is a wavelength-dependent extinction coefficient, L is the path length, and C is the analyte concentration. When working in concentration units of molarity, the Beer-Lambert Law is written as:

$$A(\lambda) = \alpha_M(\lambda) L = C \epsilon_M(\lambda) L.$$

where $\alpha_M(\lambda)$ is the wavelength-dependent molar absorption coefficient having units of cm$^{-1}$M$^{-1}$, and $\epsilon_M(\lambda)$ is the wavelength dependent molar extinction coefficient with units of liter cm$^{-1}$M$^{-1}$.

Experimental measurements are usually made in terms of transmittance (T), which is defined as:

$$T = I/I_0$$

where I is the light intensity immediately after the light passes through the sample and $I_o$ is the light intensity immediately before the light impinges on the sample. The relation between A and T is:

$$A = -\log T = -\log(I/I_o) \quad (2)$$

A working curve is a plot of the analytical signal (the instrument or detector response) as a function of analyte concentration. These working curves are obtained by measuring the signal from a series of standards of known concentration. The working curves are then used to determine the concentration of an unknown sample or to calibrate the linearity of an analytical instrument.

Modern absorption instruments can usually display the data as transmittance, %-transmittance, or absorbance. An unknown concentration of an analyte can be determined by measuring the amount of light that a sample absorbs and then applying Beer's Law. If the absorption coefficient is not known, the unknown concentration can be determined using a working curve of absorbance versus concentration derived from known standards.

Standards are materials containing a known concentration of a known analyte. They provide a reference to determine unknown concentrations or to calibrate analytical instruments. The accuracy of an analytical measurement is how close a result comes to the true value. Determining the accuracy of a measurement usually requires calibration of the analytical method with a known standard. This is often done with standards of several concentrations to make a calibration or working curve. Standard reference materials are available from standards laboratories such as the National Institute for Standards and Technology (NIST).

The linearity of the Beer-Lambert Law is limited by chemical and instrumental factors. Causes of nonlinearity include:

deviations in absorption coefficients at high concentrations (>0.01M) due to electrostatic interactions between molecules in close proximity scattering of light due to particulates in the sample fluorescence or phosphorescence of the sample changes in refractive index at high analyte concentration shifts in chemical equilibrium as a function of concentration non-monochromatic radiation (deviations can be minimized by using a relatively flat part of the absorption spectrum such as the maximum of an absorption band)

stray light

Equations (1) and (2) show that the ability of a spectrometer to detect a specific concentration depends not only on the path length through the sample, but also on the intensity noise of the light source and detector. Sensitivity can be quantified as a minimum detectable absorption loss (MDAL), i.e., the normalized standard deviation of the smallest detectable change in absorption. MDAL typically has units of $cm^{-1}$. Sensitivity is defined as the achievable MDAL in a one second measurement interval, and has units of $cm^{-1} Hz^{-1/2}$. Sensitivity accounts for the different measurement speeds achieved by diverse absorption-based methods. Sensitivity is a figure of merit for any absorption-based technique.

Typically, a spectral feature (usually called an absorption peak) of the target species is measured in order to obtain its concentration. Although many different species may absorb light at one or more wavelengths, the total spectral profile of any particular species is unique. The ability of a spectrometer to distinguish between two different species absorbing at similar wavelengths is called selectivity. Because spectral features such as absorption peaks become narrow as the sample pressure is reduced, selectivity can be improved by reducing the analyte sample operating pressure. However, the spectrometer must still be able to resolve the resulting spectral lines. Thus, selectivity depends on spectral resolution. Spectral resolution, typically measured in frequency (MHz), wavelength ($\mu m$), or wave numbers ($cm^{-1}$), is another figure of merit for a spectrometer.

Optical detection is the determination of the presence and/or concentration of one or more target species within a sample by illuminating the sample with optical radiation and measuring optical absorption by the sample. A correspondingly wide variety of optical detection methods are known. Examples of such instruments are Fourier Transform Infrared (FTIR), non-dispersive infrared, (NDIR) and tunable diode laser absorption spectroscopy (TDLAS).

None of the above-mentioned existing absorption spectroscopy methods can measure absolute absorption, regardless of whether they utilize incoherent or monochromatic light sources. Therefore, all of these approaches require calibration. Furthermore, these instruments have limited sensitivity because the gas cells they use direct the light through only a limited number of passes.

Cavity enhanced methods resolve the sensitivity limitation by increasing the effective path length. Cavity enhanced optical detection entails the use of a passive optical resonator, also referred to as a cavity. Cavity enhanced absorption spectroscopy (CEAS), integrated cavity output spectroscopy (ICOS) and cavity ring down spectroscopy (CRDS) are three of the most widely used cavity enhanced optical detection techniques. ICOS as used herein is intended to include a recent variant called off-axis ICOS where the light is injected into the resonator at an angle to the optical axis. The teaching of U.S. Pat. Nos. 5,528,040; 5,912,740; 6,795,190 and 6,466,322, which describe these techniques are hereby incorporated herein by this reference.

Cavity ring-down spectroscopy (CRDS) is based on the principle of measuring the rate of decay of light intensity inside a stable optical resonator, called the ring-down cavity (RDC). Once sufficient light is injected into the RDC from a laser source, the input light is interrupted, and the light transmitted by one of the RDC mirrors is monitored using a photodetector. The transmitted light, $I(t,\lambda)$, from the RDC is given by the equation:

$$I(t,\lambda)=I_0 e^{-t/\tau(\lambda)} \quad (3)$$

where $I_0$ is the transmitted light at the time the light source is shut off, $\tau(\lambda)$ is the ring-down time constant, and $R(\lambda)$ =$1/\tau(\lambda)$ is the decay rate. The transmitted light intensity decays exponentially over time.

In CRDS, an optical source is usually coupled to the resonator in a mode-matched manner, so that the radiation trapped within the resonator is substantially in a single spatial mode. The coupling between the source and the resonator is then interrupted (e.g., by blocking the source radiation, or by altering the spectral overlap between the source radiation and the excited resonator mode). A detector typically is positioned to receive a portion of the radiation leaking from the resonator, which decays in time exponentially with a time constant $\tau$. The time-dependent signal from this detector is processed to determine $\tau$ (e.g., by sampling the detector signal and applying a suitable curve-fitting method to a decaying portion of the sampled signal). Note that CRDS entails an absolute measurement of $\tau$. Both pulsed and continuous wave laser radiation can be used in CRDS with a variety of factors influencing the choice. The articles in the book "Cavity-Ringdown Spectroscopy" by K. W. Busch and M. A. Busch, ACS Symposium Series No. 720, 1999 ISBN 0-8412-3600-3, including the therein cited references, cover most currently reported aspects of CRDS technology.

Single spatial mode excitation of the resonator is also usually employed in CEAS(also called ICOS)) or off-axis ICOS, but CEAS differs from CRDS in that the wavelength of the source is swept (i.e., varied over time), so that the source wavelength coincides briefly with the resonant wavelengths of a succession of resonator modes. A detector is positioned to receive radiation leaking from the resonator, and the signal from the detector is integrated for a time comparable to the time it takes the source wavelength to scan across a sample resonator mode of interest. The resulting detector signal is proportional to $\tau$, so the variation of this signal with source wavelength provides spectral information on the sample. Note that CEAS/ICOS entails a relative measurement of $\tau$. The published Ph.D. dissertation "Cavity Enhanced Absorption Spectroscopy", R. Peeters, Katholieke Universiteit Nijmegen, The Netherlands, 2001, ISBN 90-9014628-8, provides further information on both CEAS and CRDS technology and applications CEAS is discussed in a recent article entitled "Incoherent Broad-band Cavity-enhanced Absorption Spectroscopy by S. Fiedler, A. Hese and A, Ruth Chemical Physics Letters 371 (2003) 284-294. The teaching of U.S. Pat. No. 6,795,190 which describes ICOS and off-axis ICOS are incorporated herein.

In cavity enhanced optical detection, the measured ring-down time depends on the total round trip loss within the optical resonator. Absorption and/or scattering by target species within the cavity normally accounts for the major portion of the total round trip loss, while parasitic loss (e.g., mirror losses and reflections from intracavity interfaces) accounts for the remainder of the total round trip loss. The sensitivity of cavity enhanced optical detection improves as the parasitic loss is decreased, since the total round trip loss depends more sensitively on the target species concentration as the parasitic loss is decreased. Accordingly, both the use of mirrors with very low loss (i.e., a reflectivity greater than 99.99 percent), and the minimization of intracavity interface reflections are important for cavity enhanced optical detection. Although the present invention will be described primarily in the context of CRDS, it should be understood that the methodology is also applicable to CEAS including ICOS and off-axis ICOS.

In the study of molecular absorption lines one must be aware that the radiation induced atomic or molecular energy level transitions are not precisely "sharp", i.e., they are not "delta functions" in wavelength. There is always a finite width to the observed spectral lines. The shape of a spectral line is described by the line profile function and its width by its full width at half maximum intensity (peak intensity) (FWHM). The physical line shape is due to the combined effects of the different broadening processes. The physical shape described by the Voigt function is known as the Voigt profile and takes into account natural broadening, Doppler broadening and pressure broadening. Line shift is the displacement of the central wavelength of the spectral line due to similar effects.

Natural broadening has its origin in the finite optical lifetime of one or both of the levels involved in a transition. Doppler broadening is due to the random motion of the emitting or absorbing atoms. A Doppler broadened line has a Gaussian shape. A Doppler shift is a line shift caused by the Doppler effect. Collisional broadening and collisional shift of the line is produced by collisions of the emitting or absorbing particle with other particles. When collisions occur between unlike, neutral particles, the term foreign-gas broadening is appropriate. When the colliding particles are of the same species, one uses the term resonance broadening. When collisions take place with charged particles or particles with a strong permanent electrical dipole moment, the term is Stark broadening. A strong chaotic electrical field causes Stark broadening, whereas an applied static electrical field induces a Stark shift.

One source of broadening is the natural line width, which arises from the uncertainty in the energy of the states involved in the transition. The Heisenberg Uncertainty Principle suggests that for particles with extremely short lifetimes, there will be a significant uncertainty in the measured energy. The numerous repeated measurements of the mass energy of an unstable particle produces a distribution of energies having a Lorentzian, or Breit-Wigner, distribution. A Lorentzian distribution resembles a Gaussian distribution near the peak, but its tails are much flatter.

If the width of this distribution at half-maximum, or full width half maximum (FWHM), is labeled $\Gamma$, then the uncertainty in energy $\Delta E$ can be expressed as:

$$\Delta E = \frac{\Gamma}{2} = \frac{\hbar}{2\zeta}$$

where the particle lifetime $\zeta$ is taken as the uncertainty in time, $\zeta = \Delta t$.

$\Gamma$ is often referred to as the "natural line width". For optical spectroscopy it is a minor factor because the natural linewidth is typically about $5 \times 10^{-4}$ cm$^{-1}$ (or $10^{-8}$ seconds or 15 MHz), a tenth as much as the Doppler broadening. At atmospheric pressures, the lines are dominated by pressure broadening. At lower pressures the dominant broadening mechanism transitions from pressure to Doppler. The natural linewidth dominates the broadening only at very low temperature and pressure.

For molecular spectra in the infrared, the limit on spectral resolution is often set by Doppler broadening. With the thermal motion of the atoms, those atoms traveling toward the detector with a velocity v will have transition frequencies which differ from those of atoms at rest by the Doppler shift, as shown in FIG. 3. The distribution can be found from the Boltzmann distribution. From the Doppler shifted wavelength, the observed frequency is:

$$v = \frac{c}{\lambda''} = \frac{v_0 \sqrt{1 - \frac{v_s^2}{c^2}}}{\left(1 - \frac{v_s}{c}\right)}$$

Rearranging gives the more convenient form:

$$v = v_0 \sqrt{\frac{1 + \frac{v_s}{c}}{1 - \frac{v_s}{c}}}$$

where the relative velocity $v_s$ is positive if the source is approaching and negative if receding.

The Maxwell speed distribution for the molecules of an ideal gas is shown in FIG. 4. Since the thermal velocities are non-relativistic, the Doppler shift in the angular frequency is given by the simple form:

$$\omega = \omega_0 \left(1 \pm \frac{v}{c}\right) \quad \omega_0 = \text{frequency for an atom at rest}$$

From the Boltzmann distribution, the number of atoms with velocity v in the direction of the observed light is given by:

$$n(v)dv = N \sqrt{\frac{m_0}{2\pi kT}} e^{-m_0 v^2 / 2kT} dv$$

where N is the total number of molecules, $m_0$ is the molecular mass, and k is Bolzmann's constant. The distribution of radiation around the center frequency is then given by:

$$I(\omega) = I_0 \exp\left[\frac{-m_0 c^2 (\omega_0 - \omega)^2}{2kT\omega_0^2}\right]$$

This is in the form of a Gaussian, and the FWHM is given by:

$$\Delta\omega_{Doppler} = \frac{2\omega_0}{c} \sqrt{2\ln 2 \frac{kT}{m_0}}$$

Often it is convenient to express this in terms of wavelength:

$$\frac{\Delta\lambda}{\lambda_0} = 2\sqrt{2\ln 2 \frac{kT}{m_0 c^2}}$$

Note that Doppler broadening is independent of the pressure and depends only on the molecular weight and the temperature of the molecules being measured. Doppler linewidths for different gases in gaseous backgrounds can range from tens of MHz to several hundred MHz.

When one moves further to longer wavelengths into the microwave region for molecular rotational spectra, the natural line width again emerges as a larger source of broadening than Doppler broadening. For infrared vibrational transitions, however, there is another form of line shape broadening that dominates at atmopheric pressure (so called "pressure broadening").

In a sample of gas, the molecules of the species of interest will be continuously colliding with themselves, as well as with molecules of the background matrix. These collisions reduce the natural lifetime, and through the uncertainty principle increase the uncertainty in energy (or spectral width). This pressure broadening results from the perturbations of rotational energy levels by molecular collisions, and can be viewed as the overlapping of the potential fields of two molecules. This type of spectral line shape broadening increases linearly with the collision rate (and thus, to a first order, with pressure) because it depends on the number of collisions per second, i.e., on the number density of the molecules. It also depends on the relative speed of the molecules, and therefore depends on the square root of the temperature. The resulting line shape is Lorentzian. The distribution of radiation around the center frequency is then given by:

$$I(\omega) = I_0 \frac{2\pi/\Delta\omega_L}{\left(\frac{\omega-\omega_0}{\Delta\omega_L}\right)^2 + \pi^2}$$

Where $\Delta\omega_L$ is the pressure broadened FWHM and $\omega_0$ is the line center. As is shown in FIG. 2, the Lorentzian line shape has wings which extend much farther than for a Gaussian line shape, and it can produce significant absorption far from line center.

The Lorentzian linewidth is in general found from:

$$\Delta\omega_L = \Delta\omega_L(STP)\frac{P\sqrt{T}}{P_L\sqrt{T_L}}$$

where $P_L$ is standard pressure (1 atm), $T_L$ is standard temperature (296° K), $\Delta\omega_L$(STP) is the Lorentzian line width at Standard Temperature and Pressure, P is the molecular number density (or pressure) and T is the sample temperature. For a system operating at constant sample temperature, the Lorentzian line width shape is simply proportional to pressure.

Note, however, that in all cases, the strength of a given transition is intrinsic to the molecule, so that the integrated intensity is conserved. If the sample is dilute in the matrix background gas, then $\Delta\omega_L$ will depend on total pressure, and the broadening will be called simply "collisional broadening". However, when the collisions of the target gas are primarily with themselves, $\Delta\omega_L$ is primarily determined by the partial pressure of the target gas, and the broadening is called "self broadening".

FIGS. 5a and 5b show the self-broadened and pressure-broadened FWHM as a function of pressure for the first overtone of HCl at 1742 nm (5577.33 cm$^{-1}$) [M De Rosa et al., Applied Physics B, vol. 72, p. 245-248 (2001)]. At constant temperature, note the linear dependence. Also note that for a typical Doppler broadening FWHM of 350 MHz at room temperature, the pressure broadening becomes comparable to the Doppler broadening at 40 Torr. From FIG. 5b it is clear that pressure broadening can strongly depend on the particular background gas. The interactions are significantly stronger for $N_2$ and $O_2$ than for Ar and He. HCl is a molecule with a large dipole moment, a quadrupole moment, and polarizabilty. While $N_2$ and $O_2$ have no dipole moment, they do have a quadrupole moment and also have a finite polarizability. The interaction is stronger for $N_2$, which has a larger quadrupole moment than $O_2$. Furthermore, the interaction of $N_2$ and $O_2$ with HCl is stronger than that of Ar and He, which have no dipole or quadrupole moment, and small polarizability. The polarizability for Ar is comparable to that of $O_2$, so that the interaction in pressure broadening is similar. However, He has a much smaller (8 times) polarizability, resulting in a much weaker pressure broadening dependence.

In general, the overall spectral lineshape at atmospheric pressure is a convolution of a Lorenztian and Doppler profile, reflecting the contributions of both pressure and Doppler broadening mechanisms. This convolution is call a Voigt profile:

$$\sigma_n(\nu) = S\frac{a}{\pi^{3/2}\alpha_D}\int_{-\infty}^{+\infty}\frac{e^{-y^2}dy}{(\delta\nu-y)^2+a^2}$$

where $\alpha = \Delta\omega_L/\Delta\omega_D$ is the damping ratio and $\delta\nu = (\nu-\nu_0)/\Delta\omega_D$.

For small damping ratios, a<<1 the line shape becomes primarily Doppler broadened, while for a>1, the line shape becomes primarily Lorentzian. In general, the Voight profile adopts a Doppler-like behavior in the line center, and a Lorentz-like behavior in the line wings. The Voight profile must be evaluated by numerical integration.

By computing the change in the Voigt profile, for example for water vapor at 1392 nm, researchers have been able to estimate that the peak absorption typically remains constant when pressure broadening is the dominant lineshape broadening mechanism. For water, the pressure broadening coefficient is linear with pressure, but the peak absorption stays almost constant between atmospheric pressure and 100 Torr (it drops only 4% in the peak although the number density of water decreases by a factor of 7.6). This is illustrated in FIGS. 6a and 6b (W. J. Kessler et al., SPIE Paper No. 3537-A30 (1998) the teaching of which is incorporated herein by this reference.

BRIEF DESCRIPTION OF THE DRAWINGS

FIGS. 6a and 6b illustrate the pressure broadening coefficient for $H_2O$ in $NH_3$ (FIG. 6a) and peak absorbance versus $NH_3$ pressure (FIG. 6b). $NH_3$ is the background and $H_2O$ is the target analyte to be measured.

FIGS. 8a, 8b and 8c show the pressure dependence of continuum background absorption and the wavelength dependence of continuum background absorption for ethylene and an ethylene-ethane gas mixture.

FIGS. 14a and 14b show detail of the spectral scan in the vicinity of two interference free $H_2S$ absorption lines as indicated in the spectrum of FIG. 13a.

FIGS. 17a, 17b and 17c also show a detailed comparison of HITRAN and measured (Meas) spectra for CO, $CO_2$ and $H_2O$ in the wavelength range of FIG. 14b. Similarly to FIGS. 16a/b/c, the differences can be clearly observed on this scale.

FIG. 18 shows the measured interference between $H_2S$ and a background multiple gas matrix in the wavelength range of FIG. 14a.

DETAILED DESCRIPTION OF THE INVENTION

To maximize sensitivity of the cavity ringdown spectrometer to a gaseous species, (i.e., the target analyte) the optical absorption at the peak of the target absorption line should be maximized. Also, to reduce interference from neighboring absorption lines of the same or other species, the width of the target and also neighboring absorption lines should be minimized. From the foregoing discussion of peak broadening, it can be seen that there exists a pressure region, which depends on the particular target species, but which can be computed from the Voight profile, using known Doppler and Lorenztian broadening coefficients, such that the peak absorption increases only slowly and/or not significantly above said pressure region, and such that the width of the target absorption line decreases only slowly and/or not significantly below said identified pressure region. This is the transition region between Doppler and pressure broadening. For practical detection applications the peak absorption and peak width are often at optimum values for analytical purposes within said transition pressure region. From example for water, in the transition region, there is only a 4% decrease in peak absorption from atmospheric pressure, while the linewidth is reduced by a factor of 6 to 7. This observation is key to selecting the appropriate spectral window for detection of a target species in a background matrix of a gas or gases that either have spectral features in proximity to the absorption features of the target species, or that have a highly absorbing background continuum absorption in the same spectral range as the absorption features of the target species.

The present invention describes a method by which the spectral window and operating pressure range are properly selected, and which allows the precise identification of the species of interest when it is present in a broadly absorbing background. The optimal detection method is a cavity-enhanced technique combined with a continuous wave (CW) tunable laser source having a narrow linewidth. Specifically, cavity ring-down spectroscopy (CRDS) or off-axis integrated cavity output spectroscopy (ICOS) using CW diode lasers or CW solid-state lasers that can operate at sub-atmospheric pressure are the optimal form of implementation for our technique.

Figure 1:
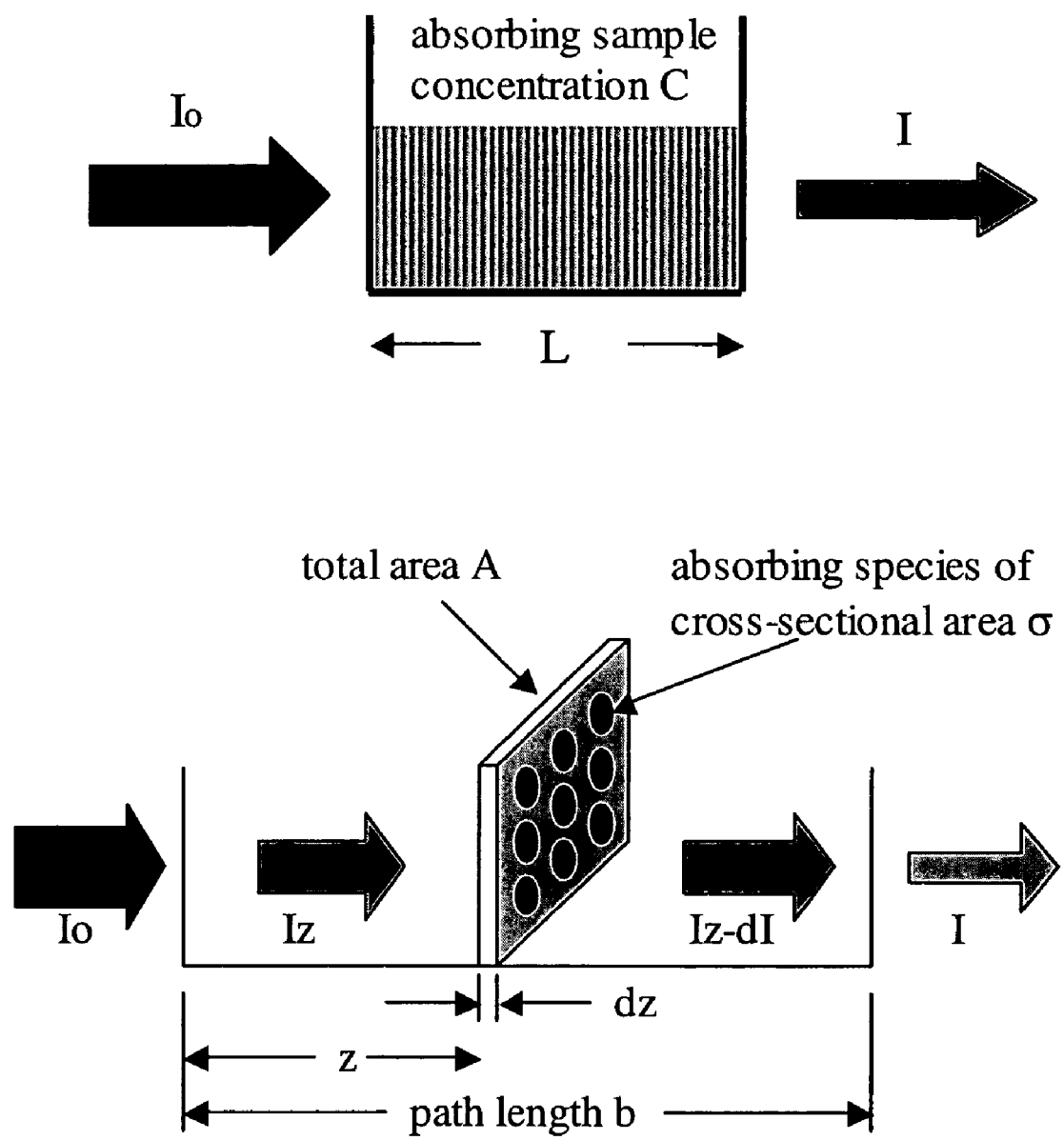
FIG. 1 illustrates one aspect of the calculation of Beer's law.
Figure 2:
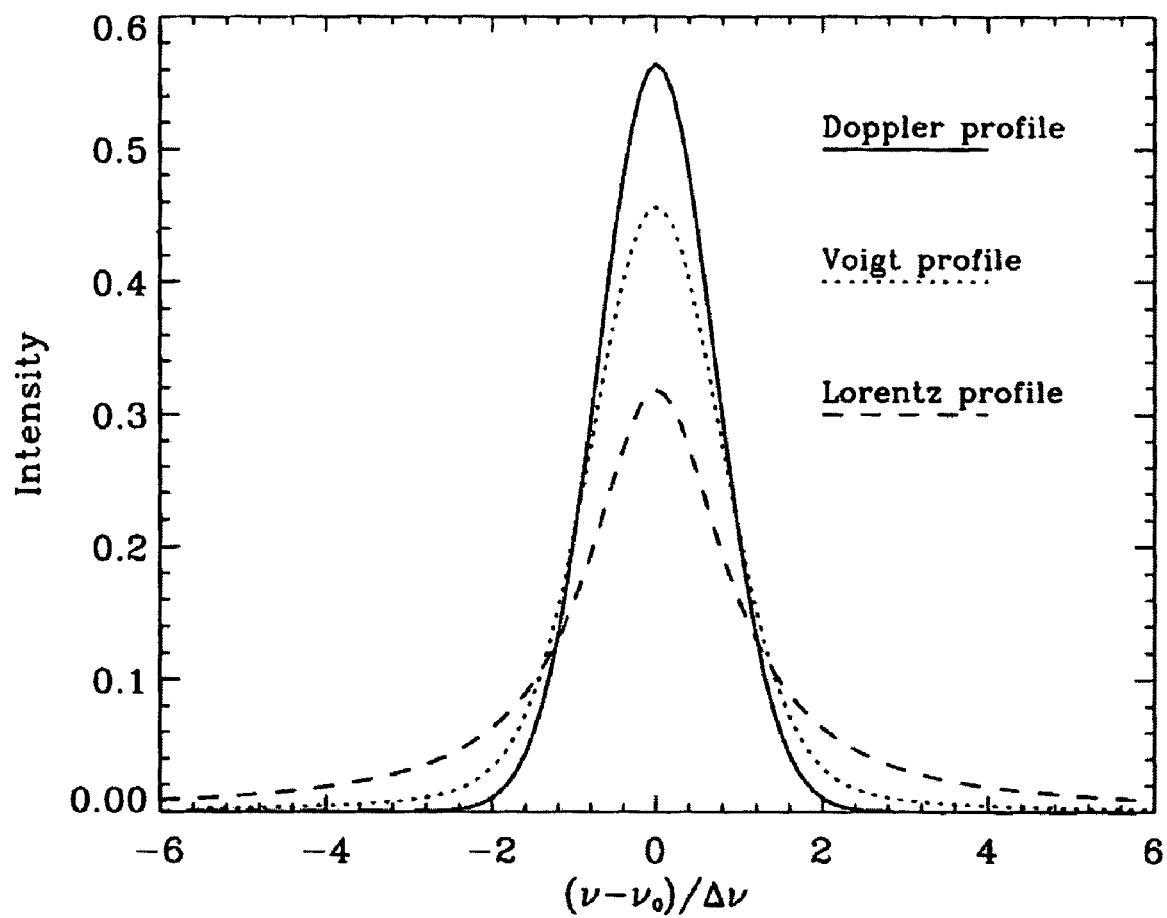
FIG. 2 compares Lorentzian, Voight and Gaussian profile distributions having the same full width half maximum value of 2.
Figure 3:
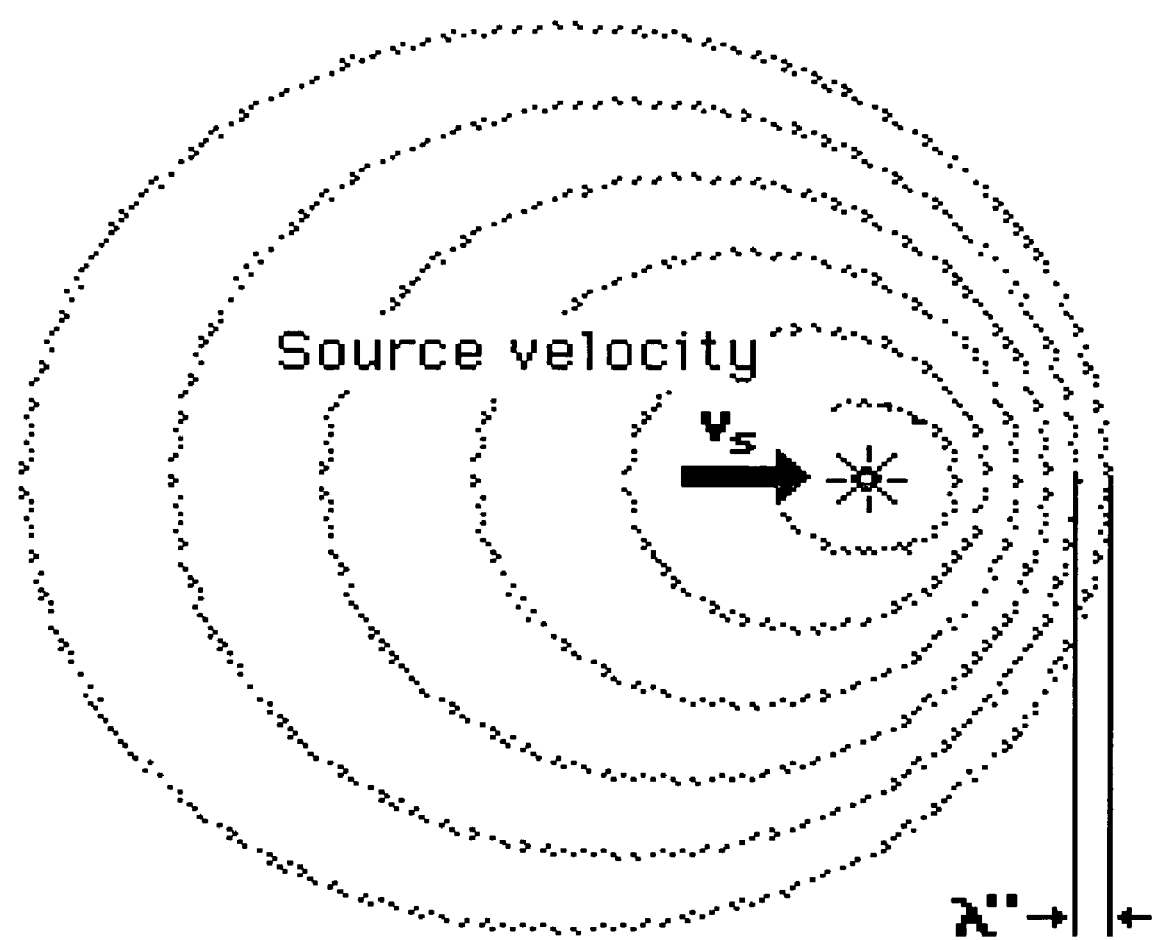
FIG. 3 is a schematic of the Doppler effect produced by thermal motion of molecules relative to the detector.
Figure 4:
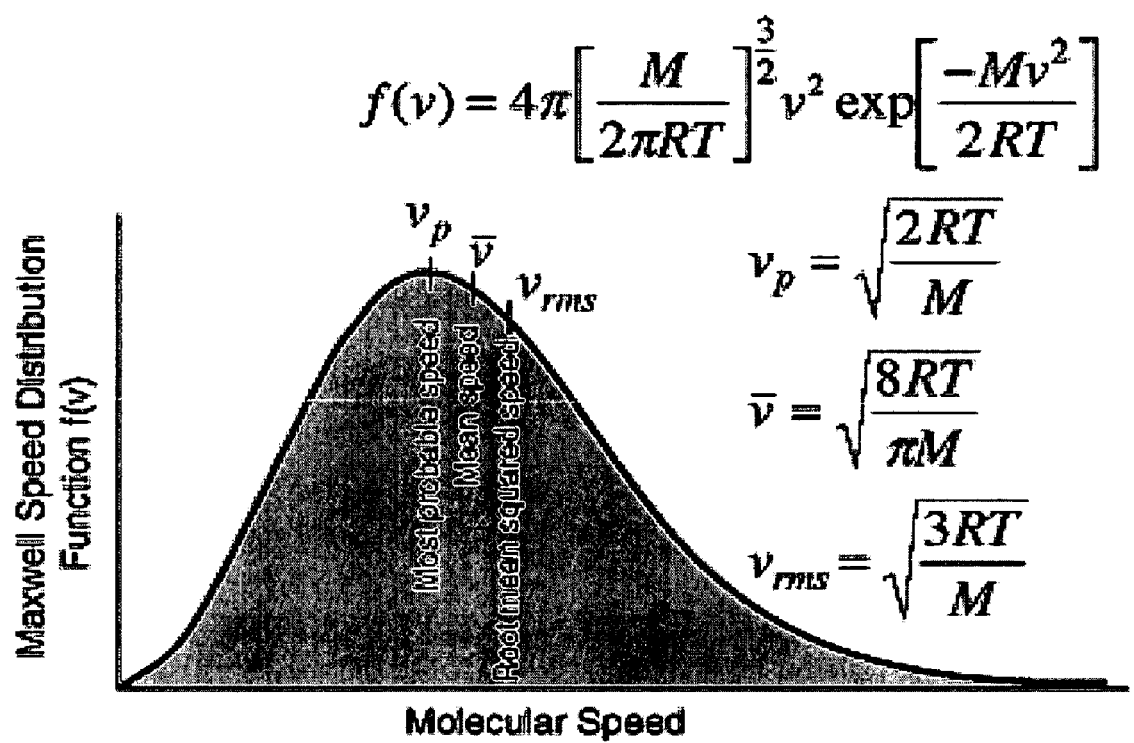
FIG. 4 shows the distribution of molecular speeds as a function of temperature and molecular mass.
Figure 5A:
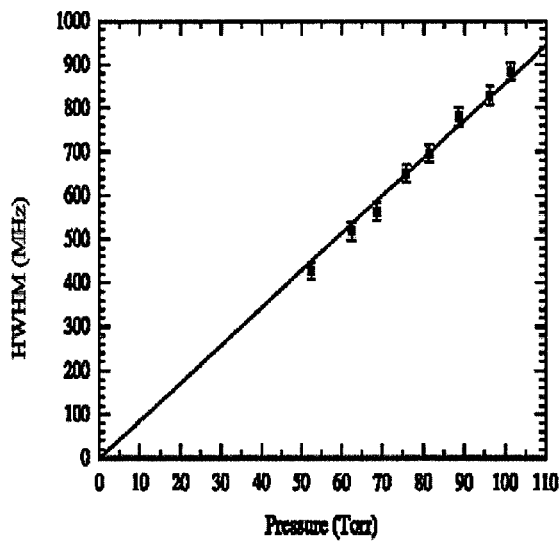
FIGS. 5a and 5b illustrate pressure broadening of $H^{35}Cl$ as a function of pressure. (a) self-broadening and (b) pressure broadening in a background of several bulk gases.
Figure 5B:
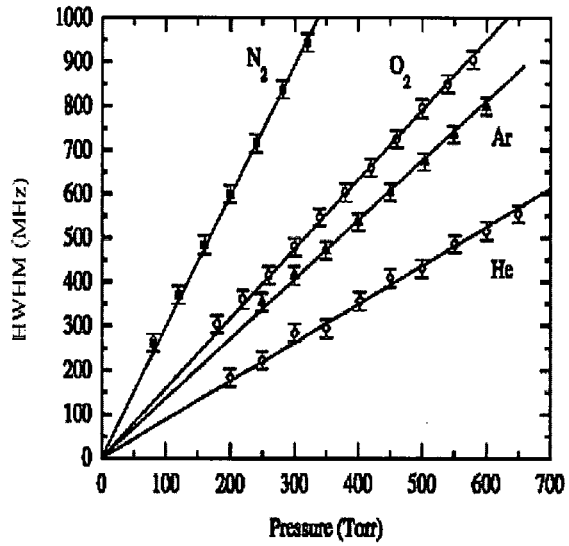
Figures 7A, 7B, 7C:
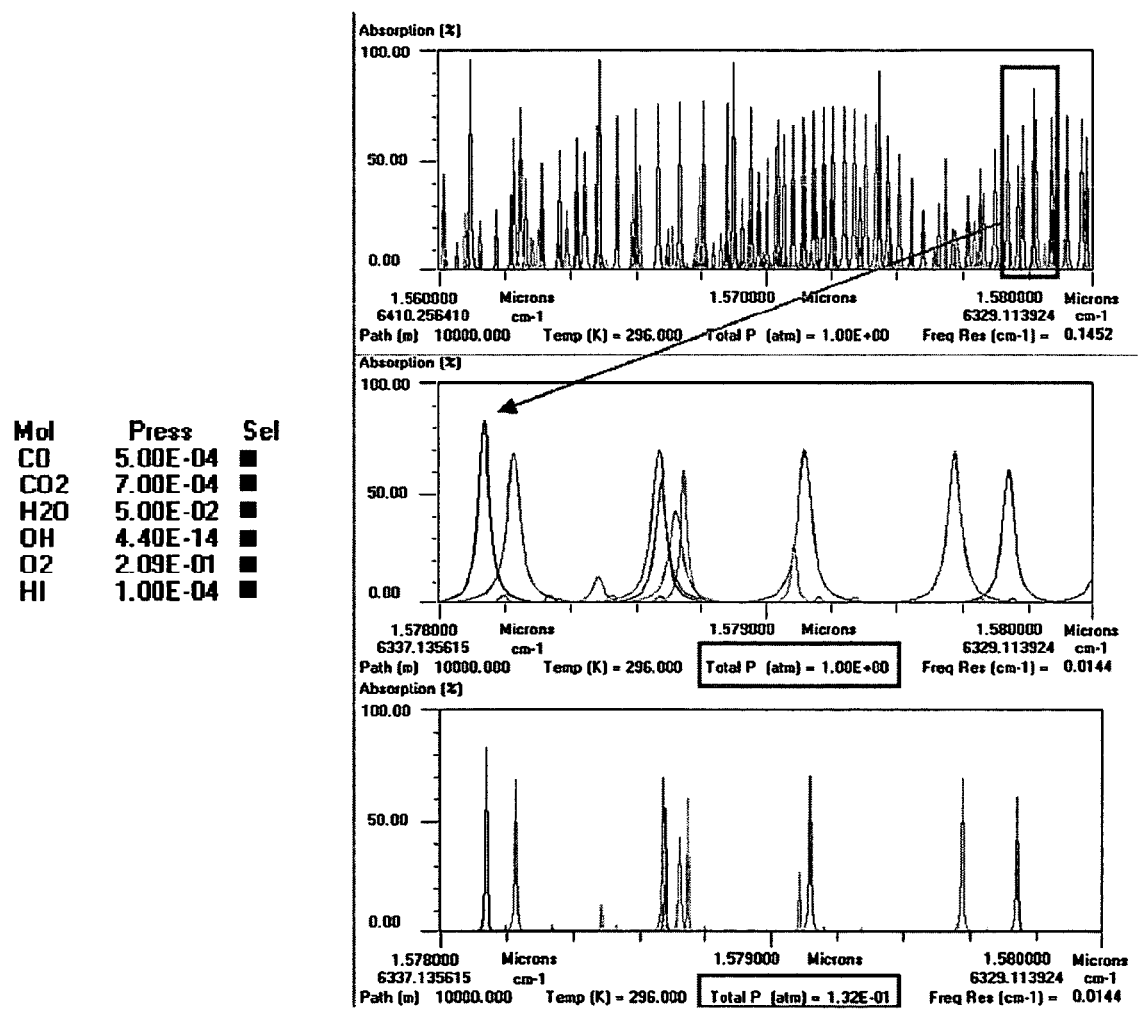
FIGS. 7a, 7b and 7c are examples of low pressure detection for improved spectroscopic selectivity.
Figure 9:
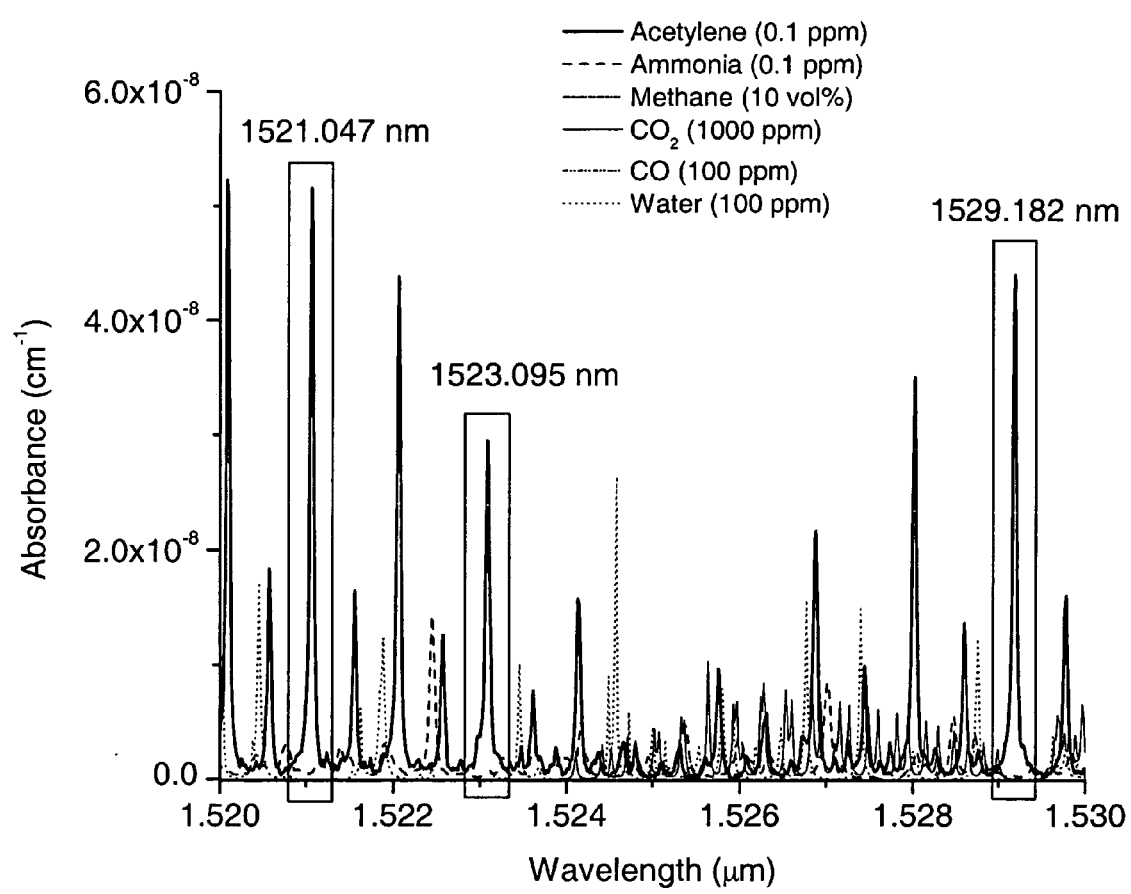
FIG. 9 shows potential interference free lines in the acetylene spectrum in the presence of the other trace impurities of CO, $CO_2$, $CH_4$, $NH_3$, and $H_2O$.

Consider, as an example, the detection of HI in a matrix of CO, $CO_2$ and $H_2O$ (such as the exhaust gases of a combustion process). FIGS. 7a, 7b and 7c show the spectral region of interest for detection (i.e., where there are strong HI lines). However, at an operating pressure of 1 atm. (FIG. 7a), all of the HI lines are significantly pressure broadened, and there are no HI absorption lines free of interference from neighboring absorption lines. FIG. 7b shows the detail of spectral lines overlapping at 1 atmosphere. However, if the operating pressure is reduced to 100 Torr, the interference is dramatically reduced, if not almost eliminated. This example illustrates how reducing the pressure improves the ability to distinguish a target species from a background matrix. It does not, however, illustrate how to select the optimal operating pressures. From FIG. 7c, the absorption of the HI feature at 100 Torr is 85% for a $10^6$ cm path length, so that the absorption coefficient is only $8.5 \times 10^{-7}$ cm$^{-1}$. Thus, a very sensitive detection method must be used in order to measure these overtones, especially if the concentration of HI is significantly lower than 100 ppm in the target application. This illustrates the need for a high sensitivity absorption technique such as CRDS or off-axis ICOS. Moreover, the method must have very high spectral resolution, because otherwise the narrowed line shapes cannot be fully resolved by the spectrometer, resulting in a loss of sensitivity and/or precision.

A similar problem can exist when trying to detect trace impurities present in essentially pure (~100%) background gases. An example is the detection of 10 ppb acetylene in pure ethylene or a "pure" combined ethane-ethylene stream. In addition to other gases interfering with the acetylene lines as was demonstrated in the HI example, the 100% background gas presents a continuum background absorption. Note that this background absorption decreases linearly with pressure. FIG. 8a illustrates background loss as a function of sample pressure. FIGS. 8b and 8c show the spectra (note the large quantity of interfering lines) of a 100% ethylene stream and an ethylene-ethane stream, respectively. Note also that the continuum absorption is different between the two process streams as a result of the presence of ethane. Note further that the continuum background absorption remains relatively high compared to the acetylene absorption line, namely $3 \times 10^{-6}$ cm$^{-1}$, even at a low operating pressure of only 10 Torr. For acetylene detection at a 10 ppb level, the background loss should not exceed $3.5 \times 10^{-6}$ cm$^{-1}$ (or 3.5 ppm/cm) to ensure that sensitivity is not compromised; therefore the system should not operate much above 10 Torr. Once this optimal operating point is established, just as in the example for HI, the appropriate spectral window for acetylene detection that provides both adequate sensitivity and selectivity can be established.

Figure 10:
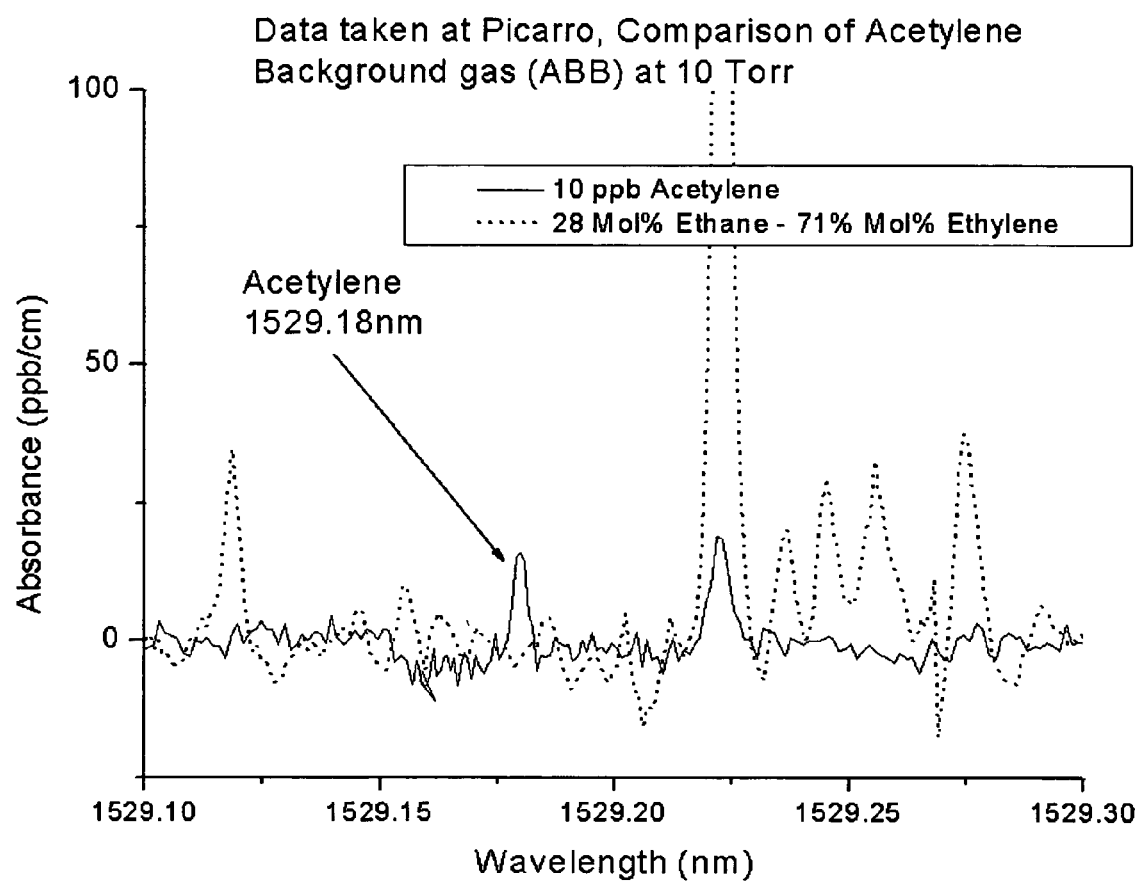
FIG. 10 shows the results of detection of acetylene in an ethane/ethylene process stream at 10 Torr.

FIG. 10 shows the detection results for acetylene in an ethane/ethylene process stream at 10 Torr. At this pressure, the background absorption of the ethylene-ethane stream becomes relatively "flattened", and the ethylene-ethane features appear separate from the target acetylene feature. The spectral feature of acetylene at 10 Torr is about 2 pm wide (i.e., 2.5 GHz) and to measure the profile of said spectral feature for identification, at least 5 spectral points, and preferably 10 spectral points, should be taken. Thus, the minimal resolution required is about 0.2 to 0.4 pm (or 250 to 500 MHz). Note that methods such as non-dispersive infrared (NDIR) spectroscopy or FTIR spectroscopy cannot achieve such spectral resolution, and more typical methods such as tunable diode laser absorption spectroscopy (TD-LAS) do not have the requisite sensitivity. TDLAS using multi-pass cells requires large volumes and is not absolutely calibrated. Photoacoustic spectroscopy is difficult to perform at pressures below several hundred Torr because the absorption signal, in the form of an acoustic wave, uses the gas itself as an acoustic transduction medium. Thus, CRDS or ICOS are the only available high resolution, high sensitivity spectroscopic techniques able to exploit said low-pressure approach to detecting trace analytes or impurities in highly absorbing background matrices.

Figure 11A:
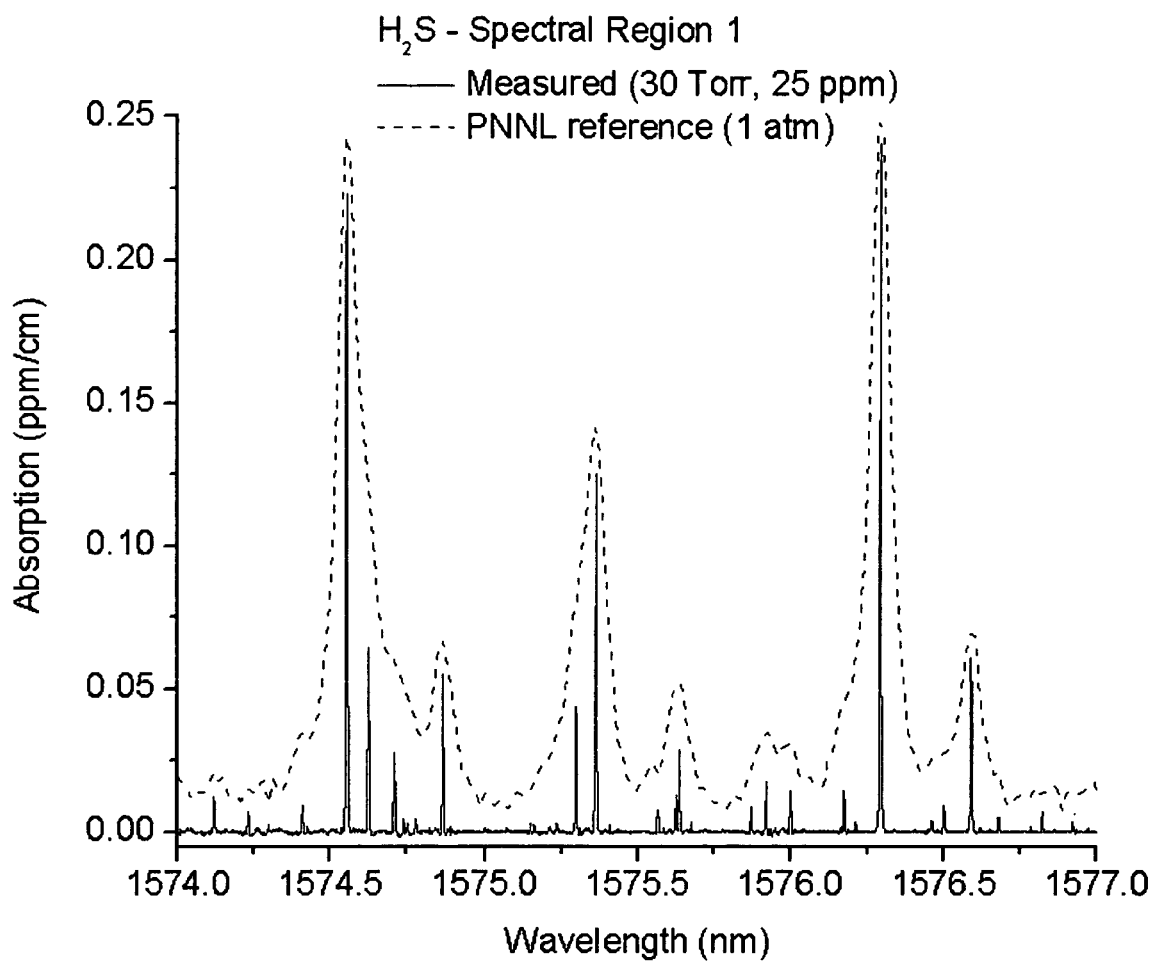
FIGS. 11a and 11b show measured spectra of $H_2S$ at a low pressure (30 Torr) compared to PNNL database spectra at high pressure (760 Torr) for two wavelength regions.
Figure 11B:
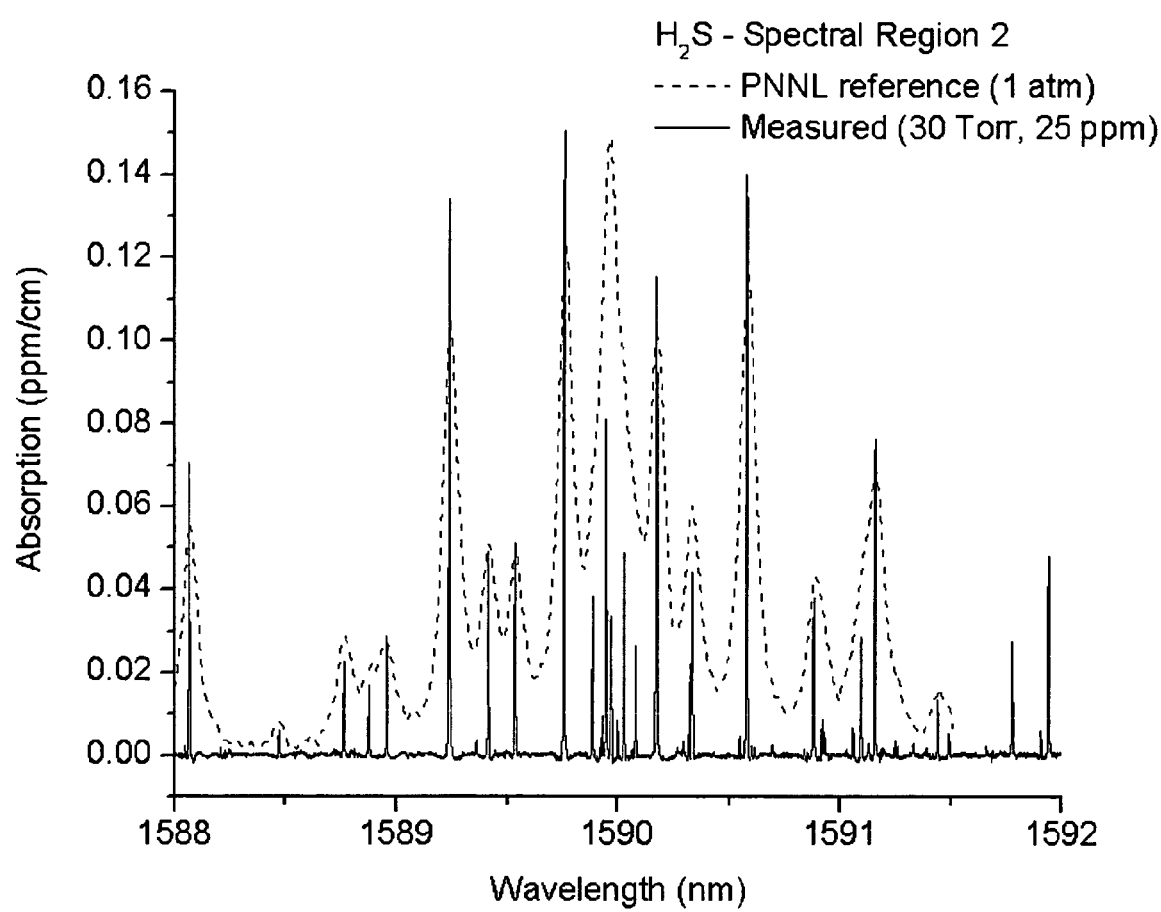

The following example, which describes the detection of a trace concentration of $H_2S$ in the presence of $CO_2$, hydrocarbons, and other gases, directly illustrates the methodology of the present invention to select an operating pressure and spectral window. The spectrum of $H_2S$ in $N_2$ was taken at 30 Torr for two wavelength regions: 1574 to 1577 nm (Region 1), and 1588 to 1592 nm (Region 2) as shown in FIGS. 11*a* and 11*b*. The CRDS spectrometer resolution was 0.001 nm, and its empty cavity decay time constant was 20.8 μs. The $H_2S$ concentration was 25 ppm. The $H_2S$ absorption features measured correspond to those given by the PNNL database.

Figure 12A:
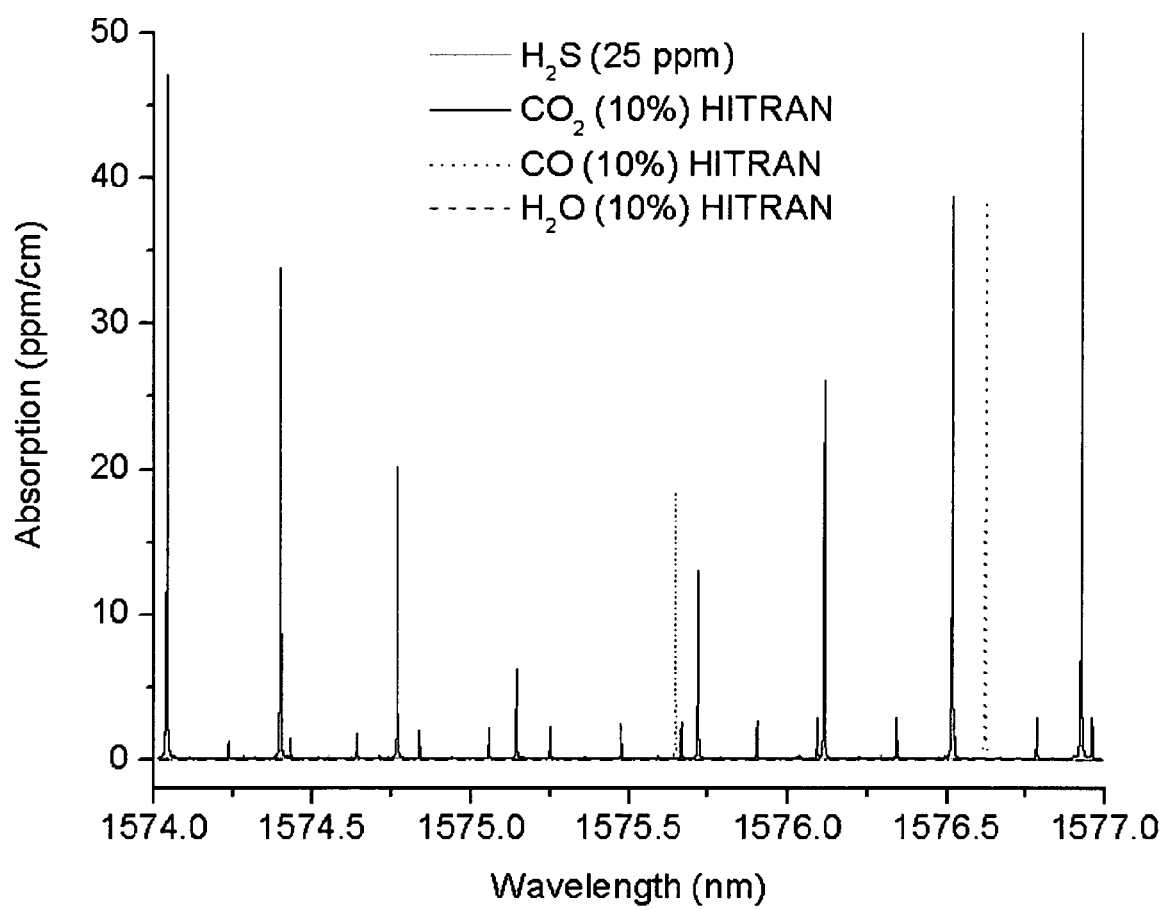
FIGS. 12a and 12b show the spectra of potential interfering species in the two wavelength regions shown in FIGS. 11a and 11b.
Figure 12B:
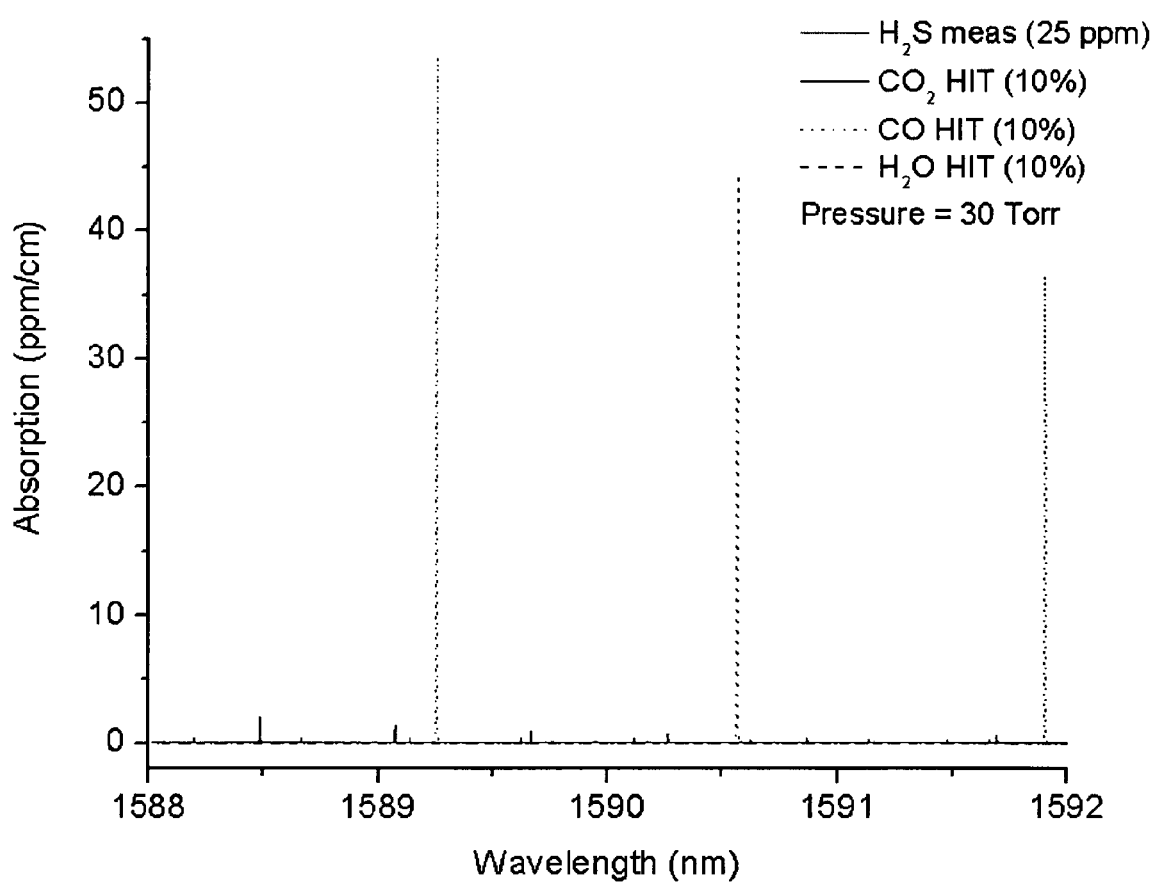
Figure 13A:
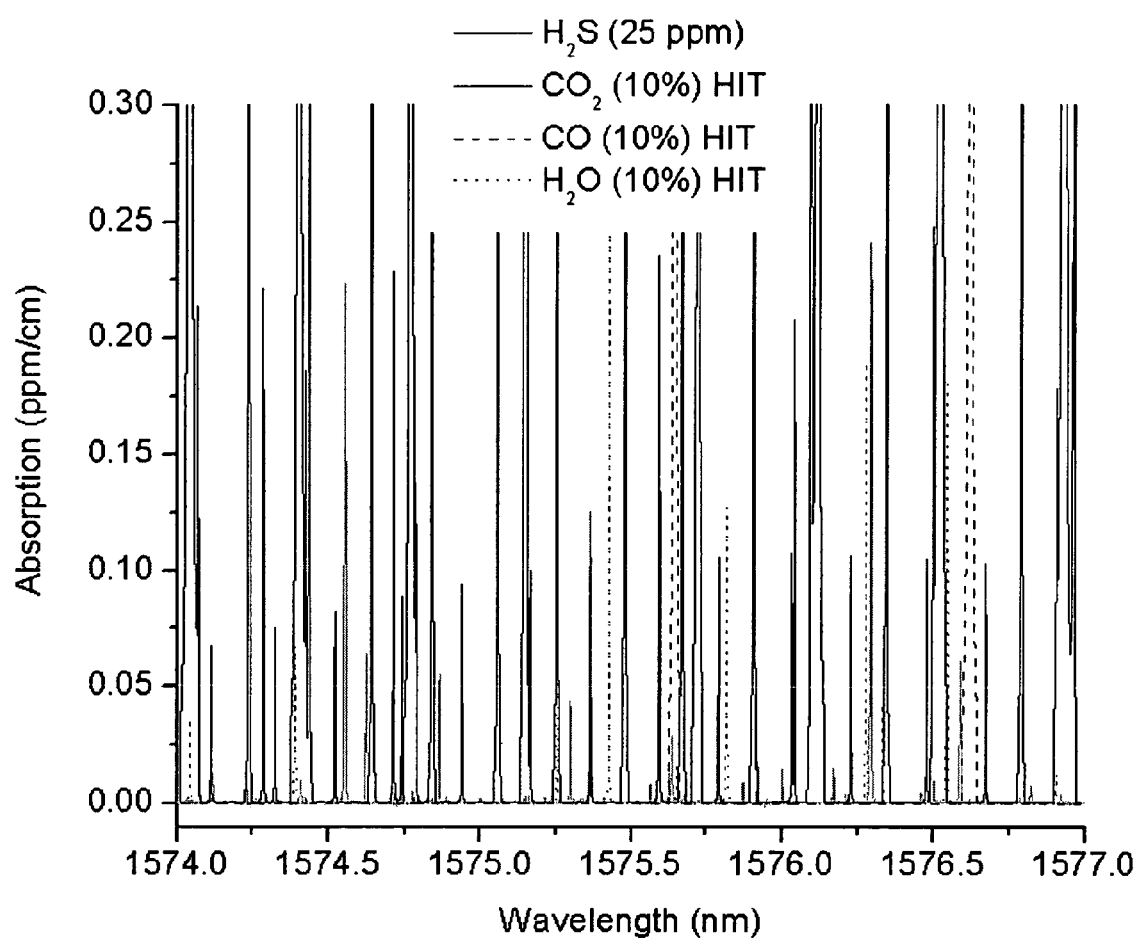
FIGS. 13a and 13b show the same spectra as in FIGS. 12a and 12b, but using an absorption scale that shows clearly the $H_2S$ absorption lines.
Figure 13B:
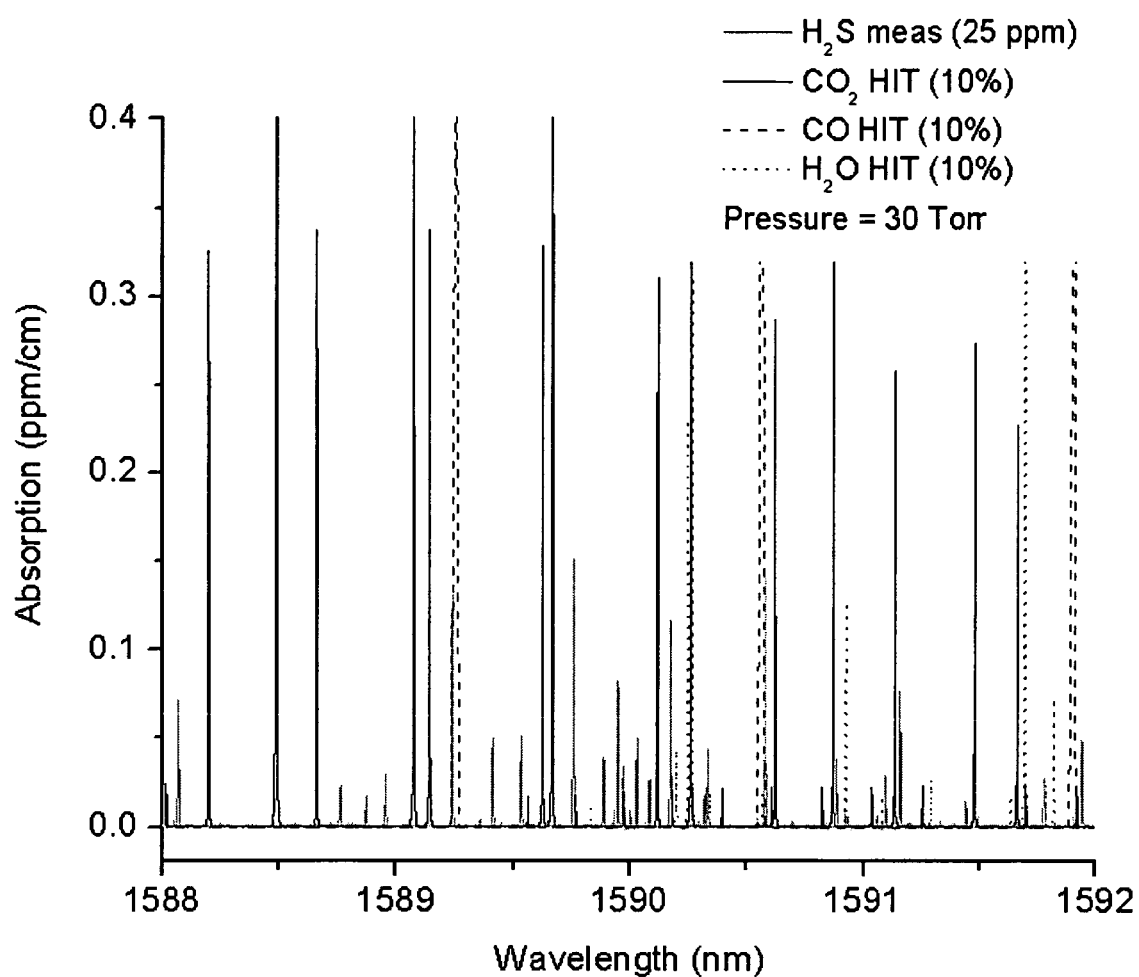
Figure 14A:
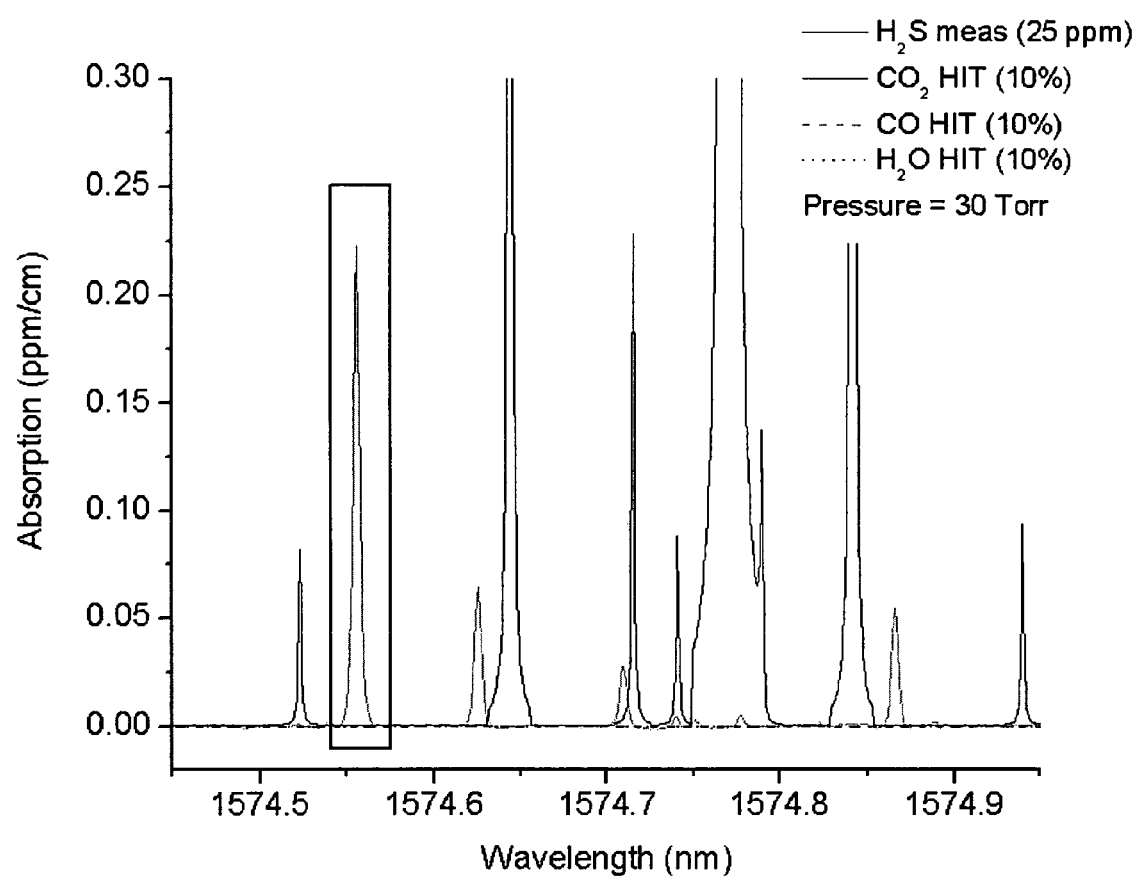
Figure 14B:
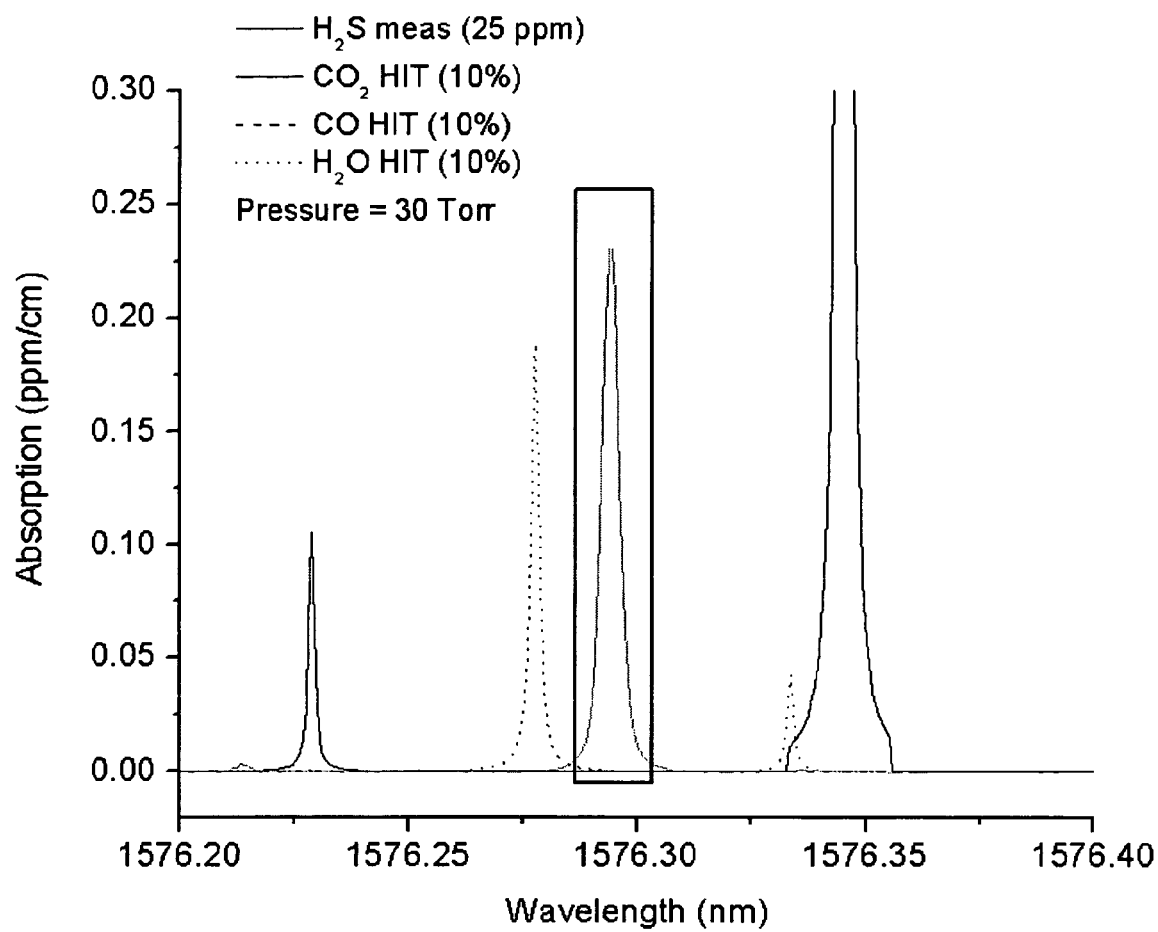
Figure 15A:
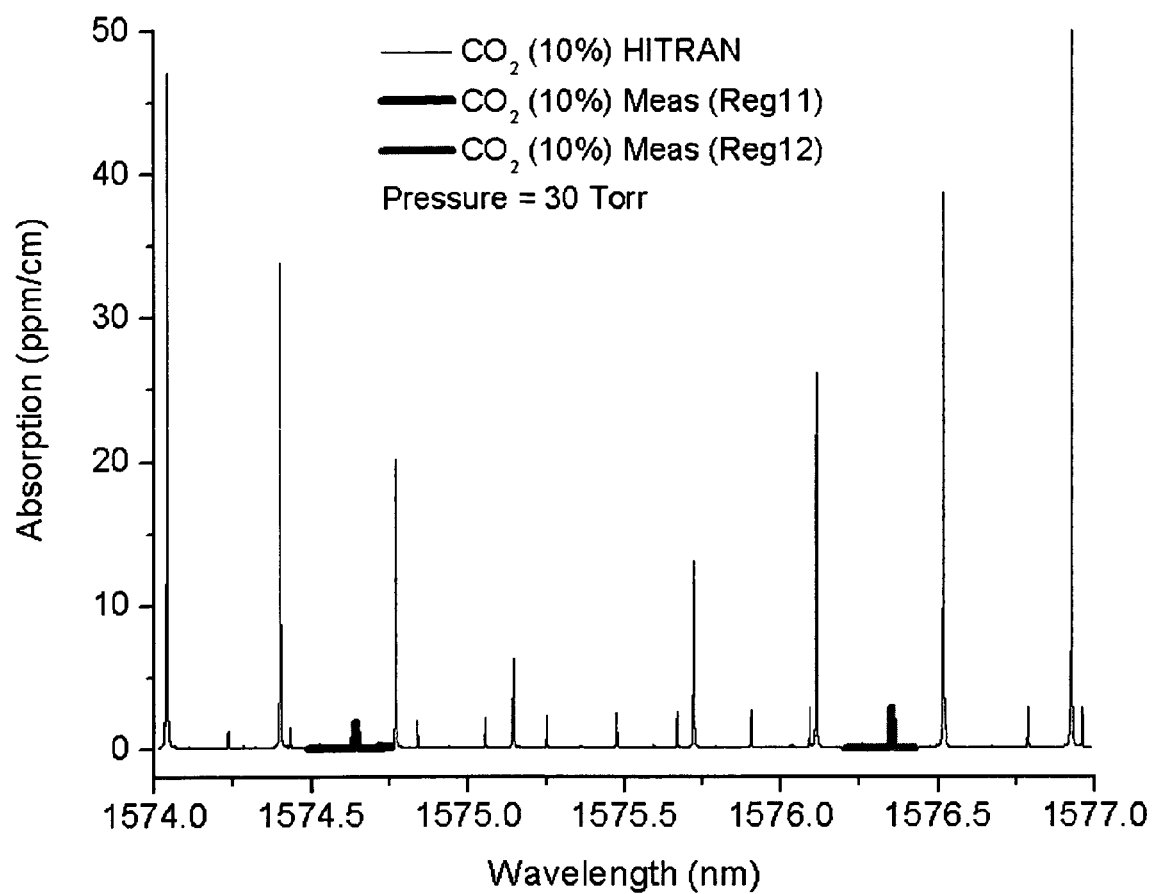
FIGS. 15a and 15b provide a comparison of HITRAN and measured (Meas) spectra in the same wavelength range as FIG. 13a for $CO_2$ (15a) and CO (15b). Note that on this scale, there are no clearly observable differences.
Figure 15B:
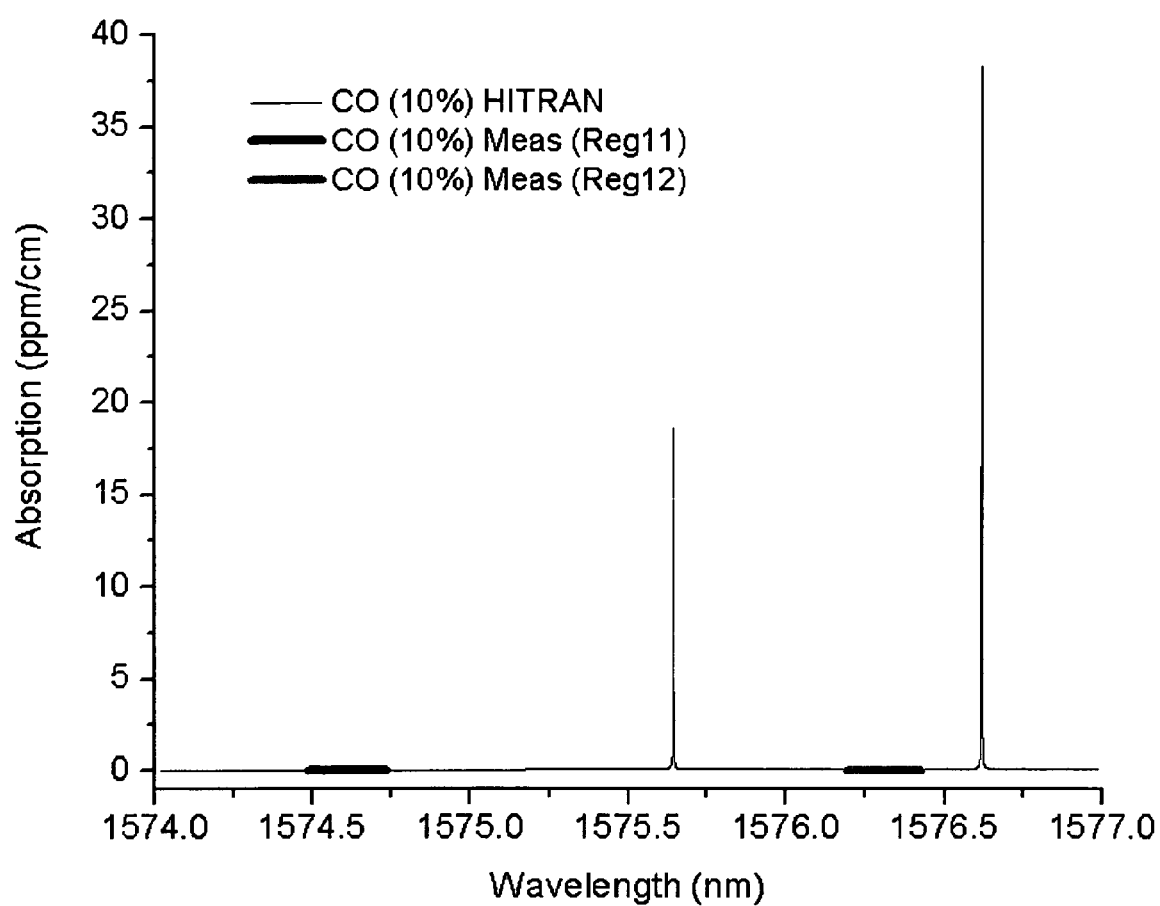
Figures 16A, 16B, 16C:
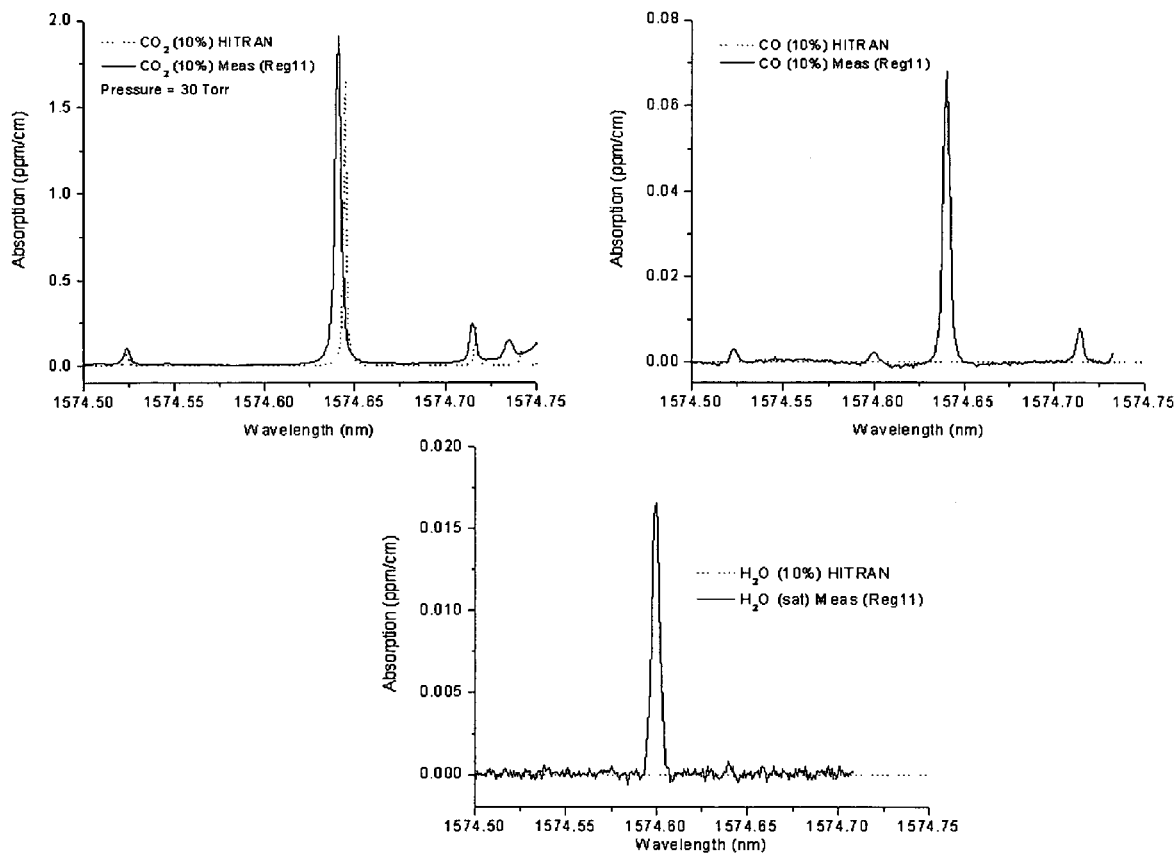
FIGS. 16a, 16b and 16c provide a detailed comparison of HITRAN and measured (Meas) spectra for CO, $CO_2$ and $H_2O$ in the wavelength range of FIG. 14a. Note that on this scale, the differences can be clearly observed.
Figure 18:
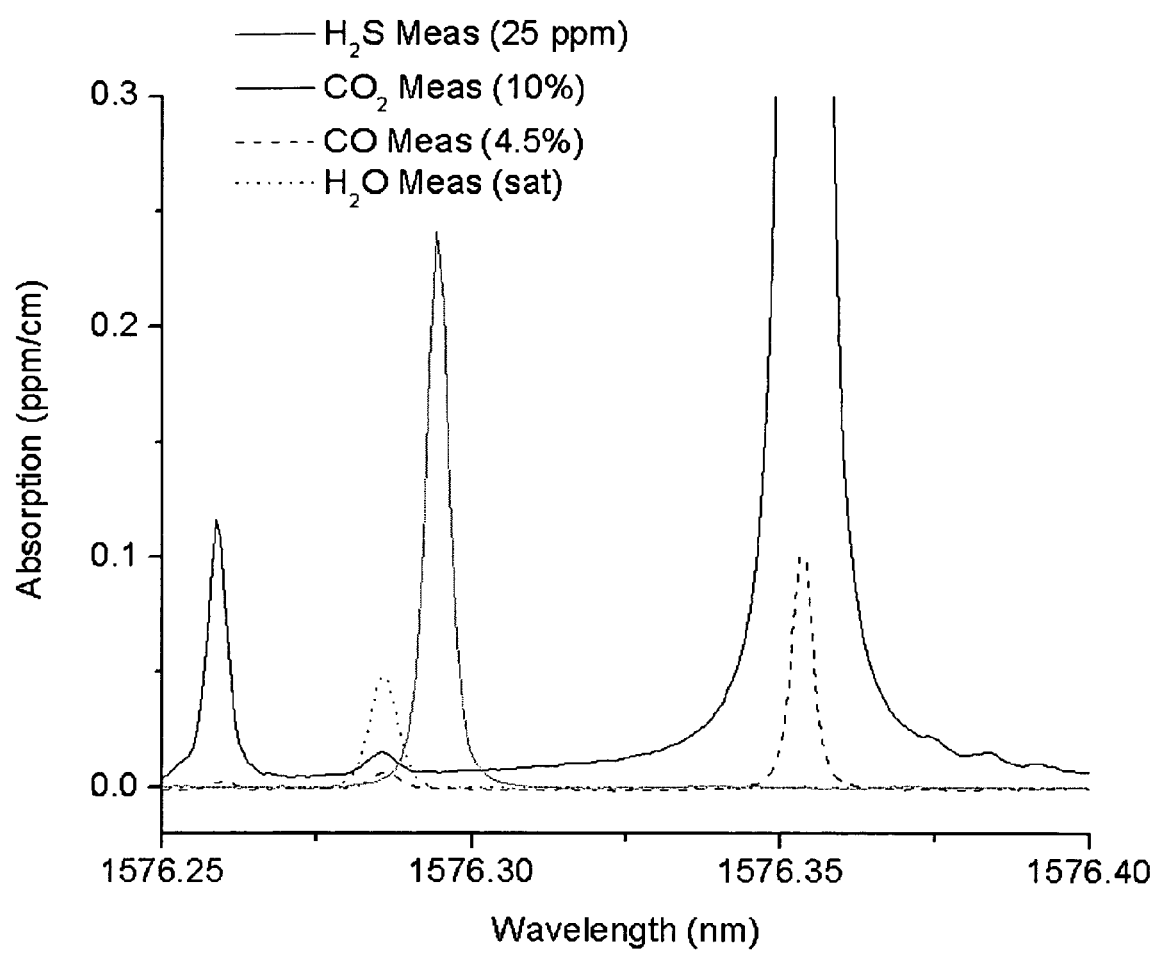

The first step is to find all potential spectral windows for the target analyte. A very low pressure (where the lines are primarily Doppler broadened) is employed to find the most suitable wavelength region where the absorption features of the target analyte are interference free from the background. In this case, the primary interfering species were identified to be CO, $CO_2$, and $H_2O$. In order to identify potential "interference-free" regions, the spectra at 30 Torr for CO, $CO_2$, and $H_2O$ at their anticipated concentrations were first simulated using HITRAN, and superposed on the low-pressure $H_2S$ spectra, as shown in FIG. 12*a* for Region 1 and 12*b* for Region 2. For Region 1, CO and $CO_2$ are the dominant absorbers, and have absorption lines that have approximately the same peak absorption. For Region 2, however, CO is the strongest absorber, while the $CO_2$ lines are weaker. In both regions, the CO and $CO_2$ peak absorptions are much greater than those of $H_2S$. FIGS. 13*a* and 13*b* show the same data as FIGS. 12*a* and 12*b* with a smaller vertical scale to examine the $H_2S$ absorption features. Region 1 yielded two wavelength ranges having potential interference-free $H_2S$ features: Region 1.1 spans 1574.5 to 1574.7 nm (FIG. 14*a*), while Region 1.2 spans 1576.2 to 1576.4 nm. Region 1.1 possesses an $H_2S$ absorption line at 1574.557 nm with a peak absorption of 0.222 ppm/cm, while Region 1.2 possesses a line at 1576.295 nm with a peak absorption of 0.243 ppm/cm. Interferences in Region 2 were seen to be significantly worse, and the interference-free lines identified for $H_2S$ in region 2 were substantially weaker than those found in Region 1. Furthermore, Region 2 shows interference from water, so that the study was focused on Region 1. (We illustrate in this example the down-selection process to find the optimal spectral window.) Experimental measurement of all three primary interferences at 30 Torr confirmed the predictions from HITRAN (FIGS. 15, 16 and 17). FIG. 18 combines the experimentally measured spectrum of $H_2S$ with all three primary interferences. The target window was down-selected to Region 1.1.

Other potential interferences were then measured in order to validate that they would not present problems. Various compounds were diluted in nitrogen, including: methane (1%), propane (1%), acetylene (102 ppm), propylene (150 ppm), n-hexane (60 ppm), toluene (100 ppm), nitric oxide (1000 ppm), and nitrogen dioxide (100 ppm). Only a very weak water peak was consistently observed in all the spectra. Therefore, these species do not have any absorption features in Region 1.1, and therefore would not be expected to interfere with $H_2S$ measurements. Note that if significant interferences were found, the search for the target spectra would be reiterated until the best window is found.

The optimal operating pressure was determined by a compromise between maximizing the peak absorption of the $H_2S$ line in Region 1.1, while minimizing its overlap with neighboring $CO_2$ lines ($CO_2$ is the dominant absorber here). The optimal pressure is selected by choosing the highest operating pressure that simultaneously maximizes the peak absorption and minimizes interferences between adjacent spectral peaks.

Figure 19:
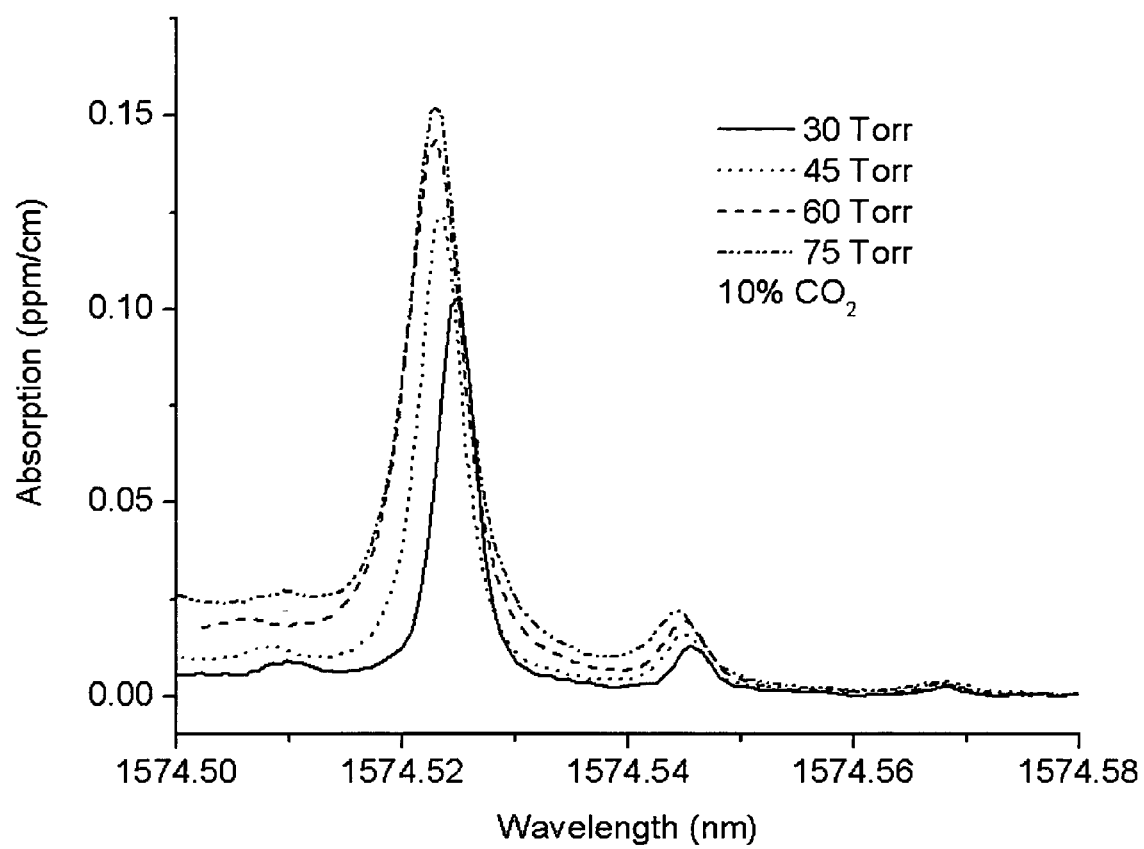
FIG. 19 shows the pressure broadening of $CO_2$ features in the wavelength range of FIG. 14a FIGS. 20a and 20b show the pressure broadening of $H_2S$ features in the wavelength range of FIG. 14a: full scan (20a) and detail (20b).
Figure 20A:
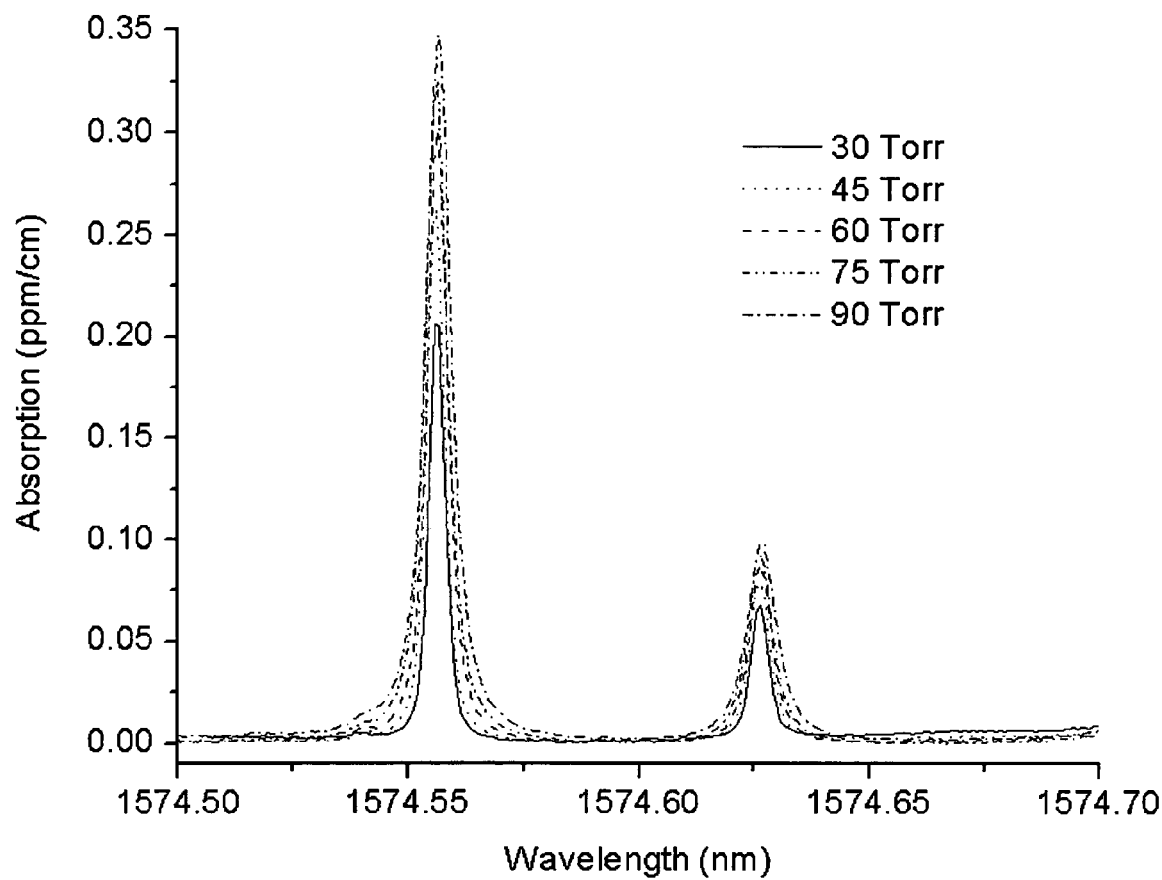
Figure 20B:
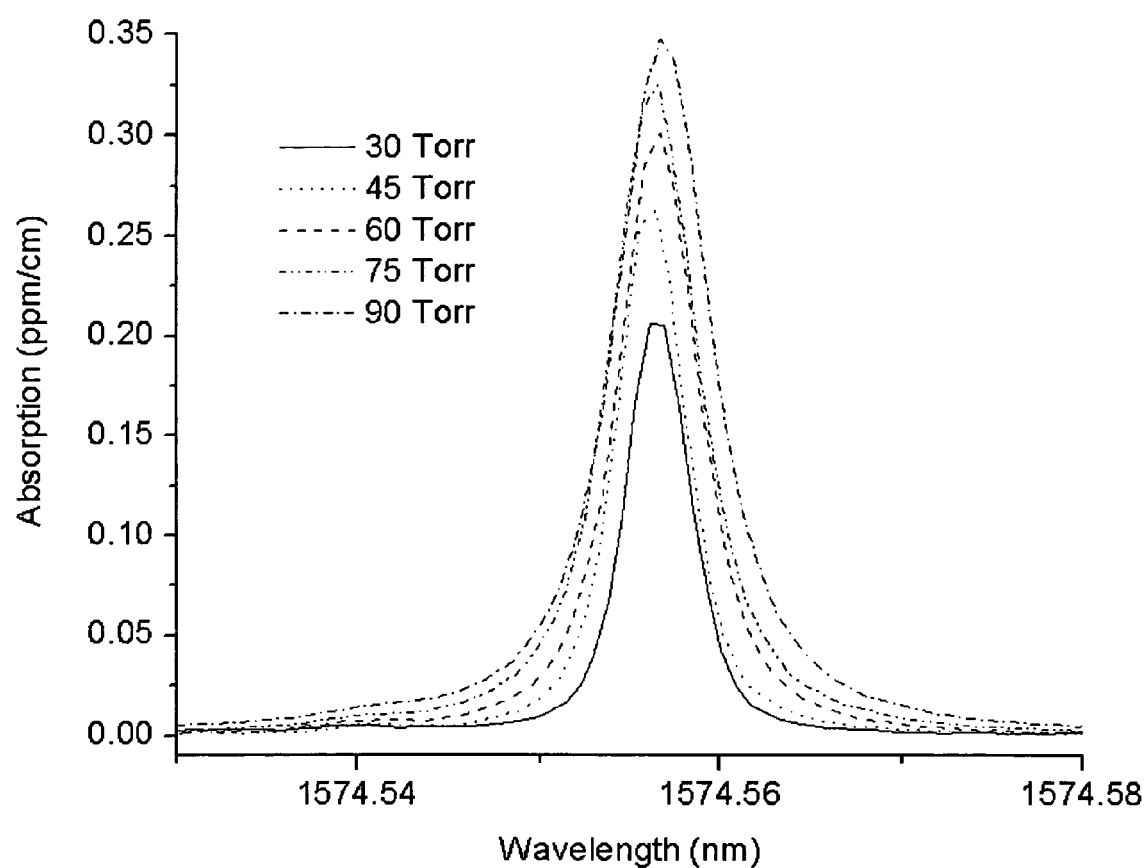

The line broadening of $H_2S$ and $CO_2$ (the dominant interference species) was studied in Region 1.1. FIGS. 19 and 20*a* and 20*b* show the changes in the absorption spectra of $CO_2$ and $H_2S$, respectively, as the operating pressure is changed. For $CO_2$, it was varied from 30 to 75 Torr, while for $H_2S$ it ranged from 30 to 90 Torr, respectively. Note the change in wavelength of the spectral features as the pressure is increased: the $CO_2$ lines become more blue-shifted (shorter wavelength), while the $H_2S$ spectra become more red-shifted (longer wavelength). Also note the increase in both peak height and peak width for the absorption features as the pressure is increased. The pressure broadening coefficients and the peak absorption were determined from the spectra as a function of pressure.

Figure 21A:
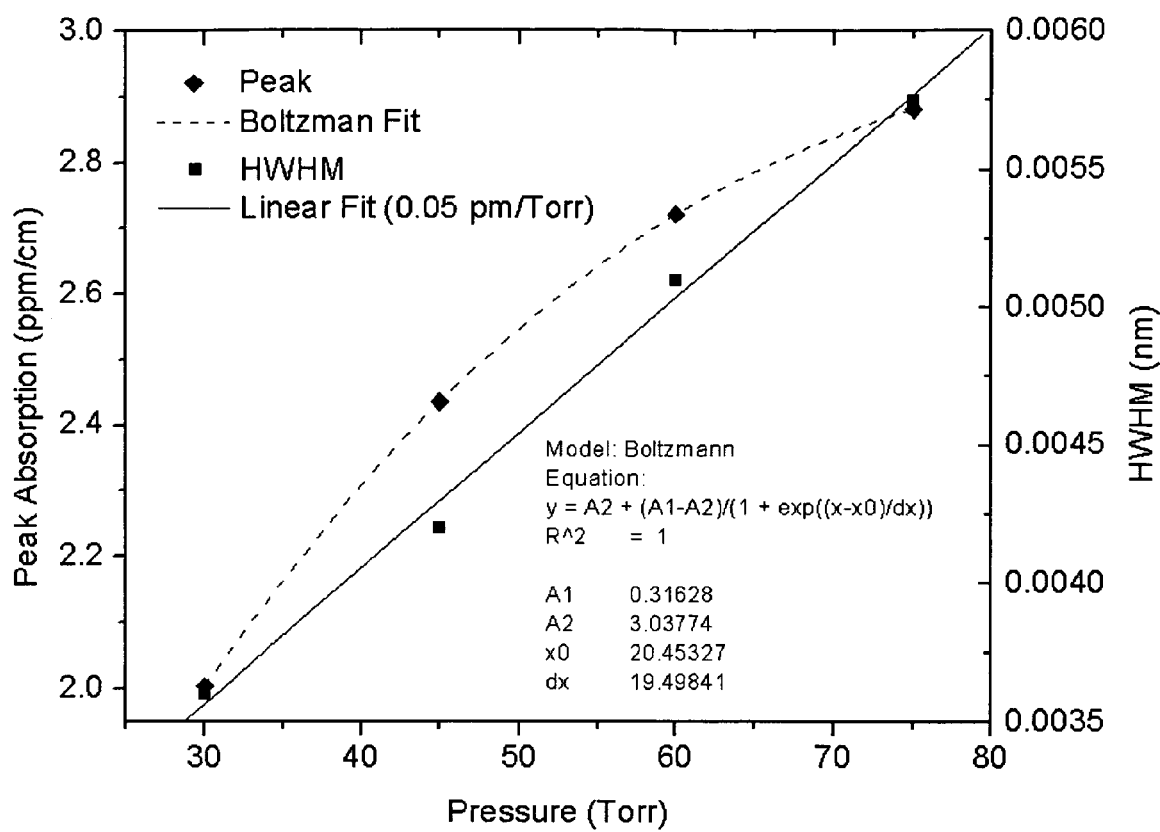
FIGS. 21a and 21b show the pressure broadening coefficients for $CO_2$ (21a) and $H_2S$ (21b).
Figure 21B:
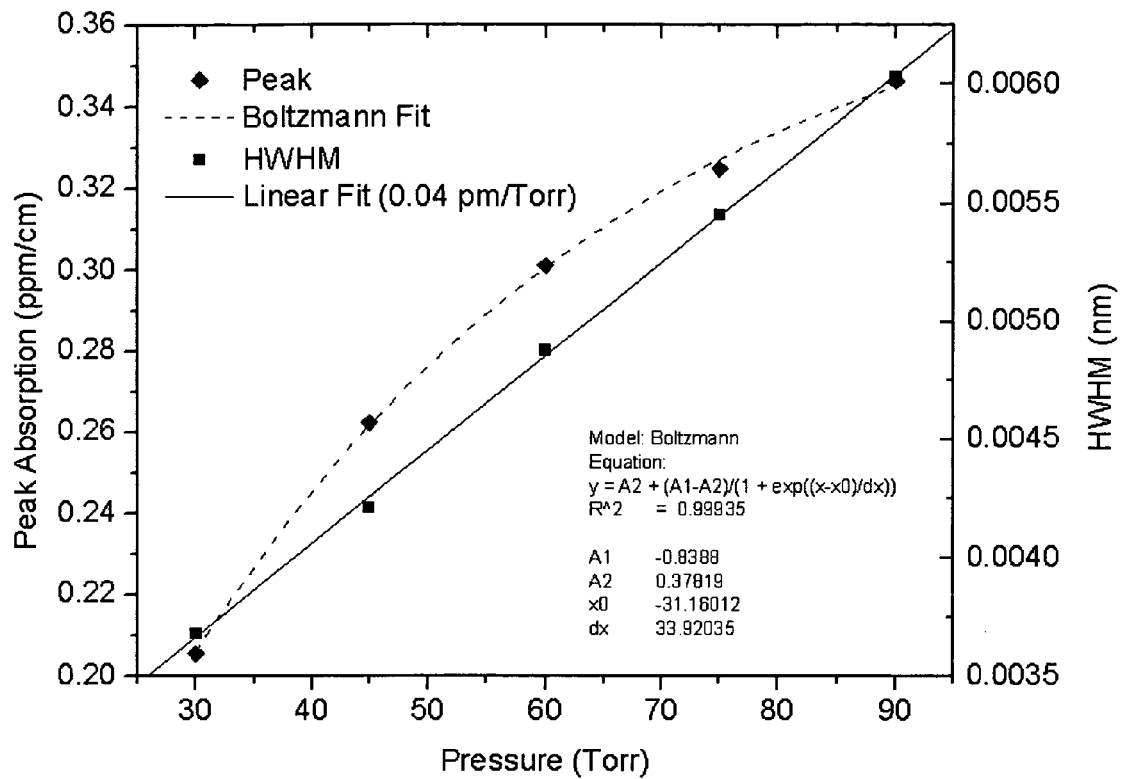

FIGS. 21*a* and 21*b* show the dependence of peak absorption and peak width on pressure for both $CO_2$ (21*a*) and $H_2S$ (21*b*). For $H_2S$, the data was taken up to 90 Torr, and the results demonstrate that the peak height starts to saturate at pressures exceeding ~100 Torr. Increasing the operating pressure beyond 100 Torr, in order to maximize the absorption peak height, therefore encounters the law of diminishing returns. There is an almost 50% increase in peak height between 30 and 60 Torr, while there is only a 15% increase between 60 and 90 Torr. The pressure broadening coefficient is slightly smaller for $H_2S$ than for $CO_2$. The line widths follow the expected linear relationship with pressure. The pressure broadening coefficient is 25% higher for $CO_2$ than $H_2S$. For a pressure increase from 30 to 60 Torr, the line width will increase about 1.5 pm (or about 187 MHz) for $CO_2$, but will only increase 1.2 pm (or about 150 MHz) for $H_2S$. The $CO_2$ lines are found at 1574.54494 nm and 1574.56771 nm, while the $H_2S$ line is found at 1574.55653 nm. At 30 Torr, the separation between the $H_2S$ line and the left and right $CO_2$ lines is 11.6 pm and 11.2 pm, respectively. An increase in pressure from 30 to 60 Torr will reduce the line separation by 2.7 pm on either side, so that 8.9 and 8.5 pm separation will still remain. However, increasing the pressure to 90 Torr will further reduce the separation to only 6.2 and 5.8 pm, which is only half of the original separation. Thus, in order to maximize selectivity, an operating pressure not exceeding 60 Torr should be chosen. A pressure of 50 to 60 Torr will maximize the $H_2S$ absorption feature height, while preserving the selectivity of the high resolution measurement by keeping the features well separated in wavelength.

The line center wavelength is also a function of the operating pressure. For $CO_2$, the lines move to shorter wavelength: the peaks both move about 0.8 pm for a 30 Torr increase in pressure, in the shorter wavelength (blue) direction. The $H_2S$ peak center moves about 0.4 pm for a 30 Torr pressure change, to longer (red) wavelengths. For a 30 to 60 Torr pressure increase, there is an additional 1.2 pm separation between the left hand $CO_2$ peak and the $H_2S$ feature, while the right hand peak and $H_2S$ feature move closer by an additional 1.2 pm. This yields a 10.1 pm separation between the $H_2S$ and left $CO_2$ peak, and a 7.3 pm separation between the $H_2S$ and right $CO_2$ peak. An operating pressure of 45 or 60 Torr is seen therefore to be a good compromise for this measurement.

Figure 22A:
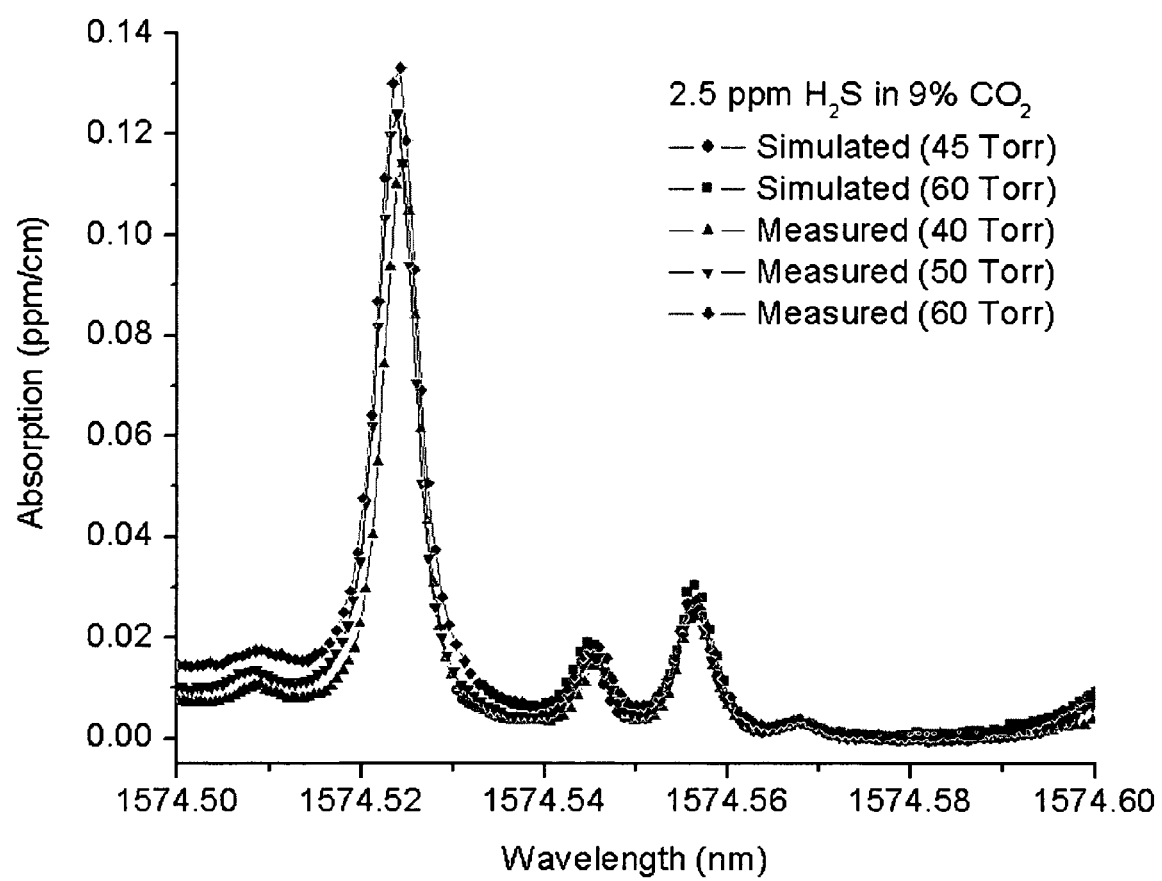
FIGS. 22a and 22b show measured and simulated spectra of $H_2S$ in $CO_2$ at several pressures.
Figure 22B:
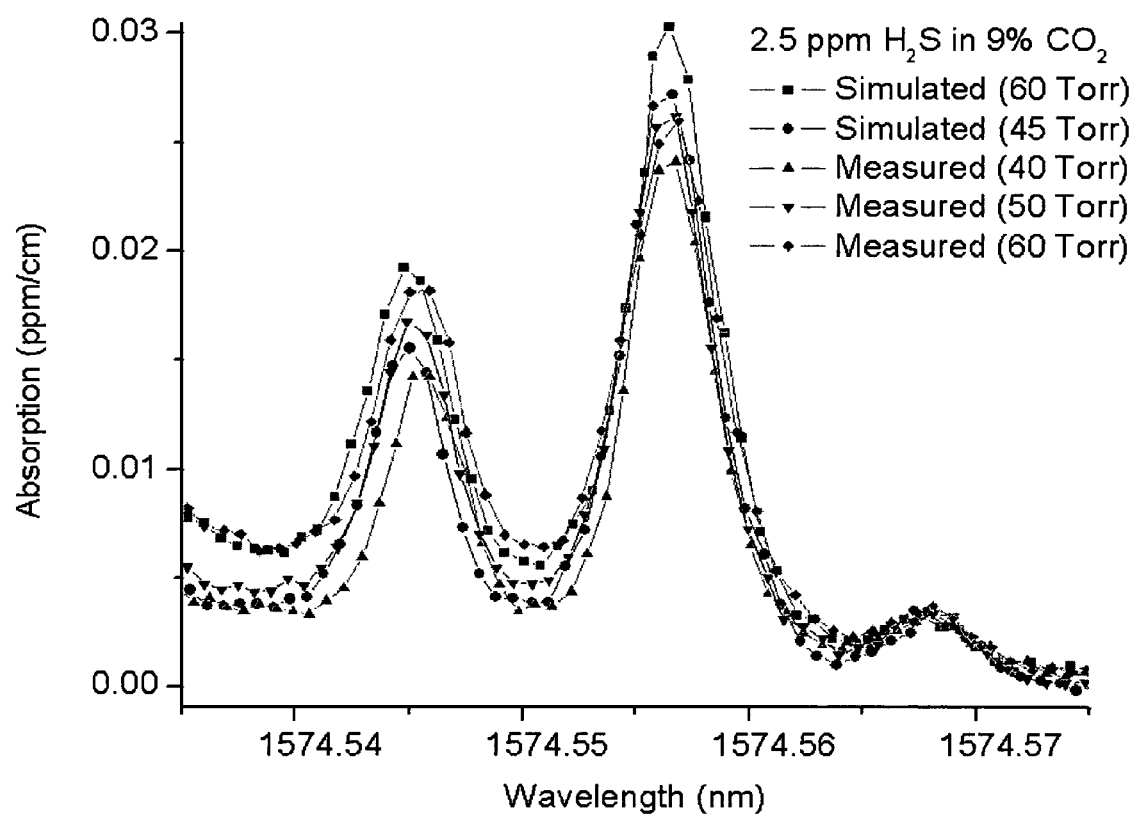

FIGS. 22a and 22b compare the measurements of $H_2S$ diluted in $CO_2$ and $N_2$ taken at different operating pressures in order to determine the optimal operating pressure. FIG. 22a shows that when the measured spectra are scaled to the closest (left) $CO_2$ feature, the $CO_2$ features scale as a function of pressure, but the $H_2S$ features still remain largely indistinguishable from each other in the pressure range of 40 to 60 Torr. However, FIG. 22b is scaled so that marked differences between the different operating pressures emerge. The data show that the peak heights are approximately equal for 50 and 60 Torr, both being larger than for 40 Torr. Furthermore, the 50 Torr data has a good compromise in peak overlap between $H_2S$ and $CO_2$: for the right $CO_2$ peak, the overlap is virtually identical to the 40 Torr data, and less than the 60 Torr data; for the left $CO_2$ peak, the overlap is significantly less than the 60 Torr data, and slightly more than the 40 Torr data. Thus, 50 Torr appears to be the optimal analysis operating pressure for this mixture. FIGS. 22a and 22b also compare the measured spectra, with "simulated" spectra obtained by scaling the $CO_2$ in $N_2$ and $H_2S$ in $N_2$ reference spectra appropriately, and adding them together. The operating pressure and spectral window were also verified experimentally.

The spectra of three concentrations (2.55 ppm, 255 ppb, and 104 ppb) of $H_2S$ in a mixture of 10% $CO_2$ in $N_2$, at 50 Torr were measured. The $H_2S$ peak is still clearly visible in the spectrum at each of these concentrations. The measurement noise was 0.22 ppb/cm of absorption. From these measurements, the resulting standard-deviation lowest detection limit (LDL) for $H_2S$ was 50 ppb concentration. For a one second detection time, it was assumed that only one spectral point would be taken, namely at the absorption peak (without measuring the baseline for reference).

Figure 23:
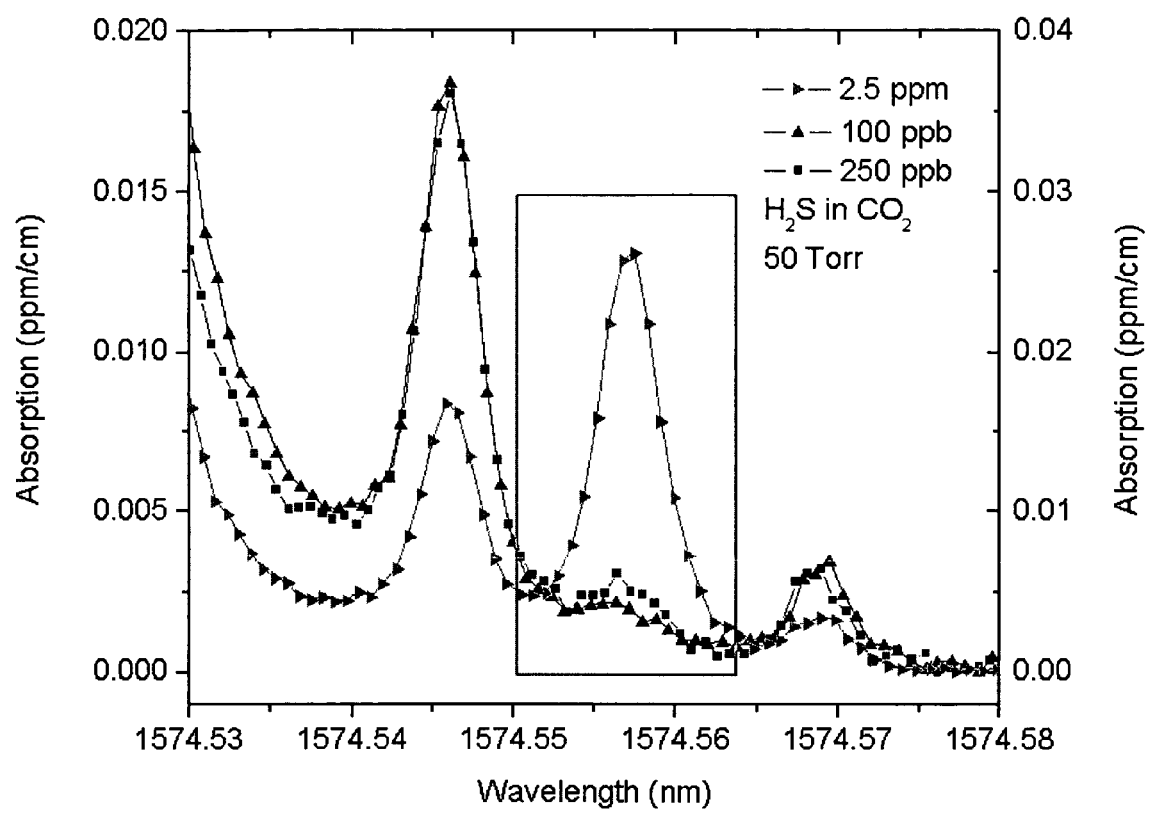
FIG. 23 shows measured $H_2S$ in $CO_2$ spectra comparing concentrations of 100 ppb, 250 ppb, and 2.5 ppm.

FIG. 23 shows the diluted $H_2S$ in $CO_2$ spectra comparing concentrations of 100 ppb, 250 ppb, and 2.5 ppm at 50 Torr. This pressure represents the best compromise to optimize performance within the spectral window selected.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general. Further, while the present invention has been particularly described in terms of certain preferred embodiments, the invention is not limited to such preferred embodiments. Rather, the scope of the invention is defined by the appended claims.

The invention claimed is:

1. A process for detecting a gaseous target analyte present as a minor constituent in an admixture with at least one other gaseous species using a cavity enhanced optical spectrometer comprising the steps of:
   i) identifying a plurality of strong spectral absorption peaks of said target analyte which are present within the scanning range of said spectrometer;
   ii) determining for said identified peaks the pressure region above which the peak width increases substantially with increasing pressure and below which the peak width is substantially independent of pressure;
   iii) determining which of the peaks identified in step i) are, within the pressure region determined in step ii), free from spectral interference by any of the other components of said admixture;
   iv) measuring the spectrum of said admixture at the pressure region identified in step ii);
   v) providing said measured spectrum as an output.

2. A process in accordance with claim 1 comprising the additional step of increasing the pressure to the maximum extent possible without causing at least one of the peaks identified in step iii) to overlap with an absorption peak of any of the other components of said admixture.

3. A process in accordance with claim 1 wherein said spectrometer utilizes as a light source at least one Distributed Bragg reflector Laser, Optical Parametric Oscillator, Optical Parametric Generator, Optical Parametric Amplifier, External Cavity Diode Laser, Distributed Feedback Laser or Quantum Cascade Laser.

4. A process in accordance with claim 3 wherein the laser used in said spectrometer is a Distributed Feedback Laser.

5. A process in accordance with claim 1 wherein at least one of the at least one other gaseous species in the admixture manifests a high continuum background absorption, further comprising identifying which of the peaks identified in step iii) minimize the background continuum and show a maximum peak height for the target analyte.

6. A process for detecting a gaseous target analyte present as a minor constituent in an admixture with at least one other gaseous species using a cavity enhanced optical spectrometer comprising the steps of:
   i) identifying a plurality of strong spectral absorption peaks of said target analyte which are present within the scanning range of said spectrometer;
   ii) determining for said identified peaks the pressure region above which the peak height is substantially independent of pressure and below which the peak height decreases substantially with decreasing pressure;

iii) determining which of the peaks identified in step i) are, within the pressure region determined in step ii), free from spectral interference by any of the other components of said admixture;

iv) measuring the spectrum of said admixture at the pressure region identified in step ii);

v) providing said measured spectrum as an output.

7. A process in accordance with claim 6 comprising the additional step of increasing the pressure to the maximum extent possible without causing at least one of the peaks identified in step iii) to overlap with an absorption peak of any of the other components of said admixture.

8. A process in accordance with claim 6 wherein said spectrometer utilizes as a light source at least one Distributed Bragg reflector Laser, Optical Parametric Oscillator, Optical Parametric Generator, Optical Parametric Amplifier, External Cavity Diode Laser, Distributed Feedback Laser or Quantum Cascade Laser.

9. A process in accordance with claim 8 wherein the laser used in said spectrometer is a Distributed Feedback Laser.

10. A process in accordance with claim 6 wherein at least one of the at least one other gaseous species in the admixture manifests a high continuum background absorption, further comprising identifying which of the peaks identified in step iii) minimize the background continuum and show a maximum peak height for the target analyte.

11. A process for detecting a gaseous target analyte present as a minor constituent in an admixture with at least one other gaseous species using a cavity enhanced optical spectrometer comprising the steps of:

i) identifying a plurality of strong spectral absorption peaks of said target analyte which are present within the scanning range of said spectrometer;

ii) determining for said identified peaks the pressure region above which the peak width increases substantially with increasing pressure and below which the peak width is substantially independent of pressure;

iii) determining if any of the peaks identified in step i) are, within the pressure region determined in step ii), free from spectral interference by absorption peaks of any of the other components of said admixture, and if none of said identified peaks are interference free, reducing the pressure to an extent sufficient to minimize overlap with the interfering absorption peaks;

iv) measuring the spectrum of said admixture at the pressure region identified in step ii);

v) providing said measured spectrum as an output.

12. A process in accordance with claim 11 wherein said spectrometer utilizes as a light source at least one Distributed Bragg reflector Laser, Optical Parametric Oscillator, Optical Parametric Amplifier, Optical Parametric Generator, External Cavity Diode Laser, Distributed Feedback Laser or Quantum Cascade Laser.

13. A process in accordance with claim 12 wherein the laser used in said spectrometer is a Distributed Feedback Laser.

14. A process in accordance with claim 11 wherein at least one of the at least one other gaseous species in the admixture manifests a high continuum background absorption, further comprising identifying which of the peaks identified in step iii) minimize the background continuum and show a maximum peak height for the target analyte.

\* \* \* \* \*